US009855341B2

(12) United States Patent
Li et al.

(10) Patent No.: US 9,855,341 B2
(45) Date of Patent: Jan. 2, 2018

(54) FORMULATIONS AND CARRIER SYSTEMS INCLUDING FARNESYLTHIOSALYCYLIC MOITIES

(71) Applicant: University of Pittsburgh—Of the Commonwealth System of Higher Education, Pittsburgh, PA (US)

(72) Inventors: Song Li, Wexford, PA (US); Yixian Huang, Pittsburgh, PA (US); Xiaolan Zhang, Pittsburgh, PA (US); Xiang Gao, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/625,873

(22) Filed: Feb. 19, 2015

(65) Prior Publication Data
US 2015/0231271 A1    Aug. 20, 2015

Related U.S. Application Data

(60) Provisional application No. 61/941,998, filed on Feb. 19, 2014.

(51) Int. Cl.
| | |
|---|---|
| A61K 47/48 | (2006.01) |
| A61K 31/337 | (2006.01) |
| A61K 31/235 | (2006.01) |
| A61K 31/704 | (2006.01) |
| A61K 9/00 | (2006.01) |
| A61K 9/107 | (2006.01) |
| C08G 65/331 | (2006.01) |
| C08G 65/333 | (2006.01) |
| C08G 65/334 | (2006.01) |

(52) U.S. Cl.
CPC ...... *A61K 47/48215* (2013.01); *A61K 9/0019* (2013.01); *A61K 9/1075* (2013.01); *A61K 31/235* (2013.01); *A61K 31/337* (2013.01); *A61K 31/704* (2013.01); *C08G 65/331* (2013.01); *C08G 65/334* (2013.01); *C08G 65/3311* (2013.01); *C08G 65/3344* (2013.01); *C08G 65/33306* (2013.01); *C08G 65/33396* (2013.01); *C08L 2203/02* (2013.01)

(58) Field of Classification Search
CPC .......... A61K 47/48215; A61K 31/337; A61K 31/235; A61K 31/704; A61K 9/0019; A61K 9/1075; C08G 65/331; C08G 65/3311; C08G 65/33306; C08G 65/33396; C08G 65/334; C08L 2203/02
See application file for complete search history.

(56) References Cited

U.S. PATENT DOCUMENTS

| | | |
|---|---|---|
| 2011/0065807 A1 | 3/2011 | Radovic-Moreno |
| 2011/0117024 A1 | 5/2011 | Sinko |
| 2012/0309780 A1 | 12/2012 | Kwon |

FOREIGN PATENT DOCUMENTS

| | | |
|---|---|---|
| WO | WO9513059 A1 | 5/1995 |
| WO | WO2013152227 A1 | 10/2013 |

OTHER PUBLICATIONS

Xiaolan Zhang, et al, PEG-Farnesylthiosalicylate Conjugate as a Nanomicellar Carrier for Delivery of Paclitaxel, 24 Bioconjugate Chem. 464 (Feb. 20, 2013).*

Chen, Y., et al. Targeted delivery of curcumin to tumors via PEG-derivatized FTS-based micellar system. The AAPS journal 16, 600-608 (2014).

Zhang, X., et al. PEG-farnesyl thiosalicylic acid telodendrimer micelles as an improved formulation for targeted delivery of paclitaxel. Molecular pharmaceutics 11, 2807-2814 (2014).

Zhang, X., et al. Reduction-sensitive dual functional nanomicelles for improved delivery of paclitaxel. Bioconjugate chemistry 25, 1689-1696 (2014).

(Continued)

Primary Examiner — Sean M Basquill
(74) Attorney, Agent, or Firm — Bartony & Associates, LLC

(57) ABSTRACT

A method of forming or creating a formulation for a compound to be delivered includes creating a carrier agent by conjugating at least one hydrophobic domain or hydrophobic compound with at least one hydrophilic domain or hydrophilic compound and associating the compound to be delivered with the carrier agent to create the formulation. The at least one hydrophobic compound has the formula:

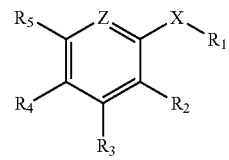

wherein R1 is a farnesyl group, a geranyl group or geranylgeranyl group, X is O, S, SO, $SO_2$, NH or Se, Z is C—$R_2$ or N, $R_2$ is H, CN, $CO_2R_7$, $SO_3R_7$, $CONR_7R_8$ or $SO_2NR_7R_8$, wherein $R_7$ and $R_8$ are each independently H, an alkyl group, an alkenyl group, $CO_2M$ or $SO_3M$, wherein M is a cation and $R_3$, $R_4$, and $R_5$ are independently H, a carboxyl group, an alkyl group, an alkenyl group, an aminoalkyl group, a nitroalkyl group, a nitro group, a halo atom, an amino group, a mono-alkylamino group, a di-alkylamino group, mercapto group, a mercaptoalkyl group, an azido group or a thiocyanato group. A plurality of the carrier agents are adapted to assemble into a structure. The hydrophobic compound is cleavably conjugated to the at least one hydrophilic compound via a linkage which is labile in vivo.

25 Claims, 20 Drawing Sheets

(56) References Cited

OTHER PUBLICATIONS

Zhang, P., et al. A PEG-Fmoc conjugate as a nanocarrier for paclitaxel. Biomaterials 35, 7146-7156 (2014).
Zhang, X., et al. Targeted delivery of anticancer agents via a dual function nanocarrier with an interfacial drug-interactive motif. Biomacromolecules 15, 4326-4335 (2014).
Zhang, X., et al. Tunable pH-Responsive Polymeric Micelle for Cancer Treatment. ACS Macro Letters 4, 620-623 (2015).
Sun, J., et al. A prodrug micellar carrier assembled from polymers with pendant farnesyl thiosalicylic acid moieties for improved delivery of paclitaxel. Acta Biomaterialia 43, 282-291 (2016).
Wolfson, E., et al. Enhancing FTS (Salirasib) efficiency via combinatorial treatment. Biology of the cell 107, 130-143 (2015).
Zhang, X., et al. PEG-famesylthiosalicylate conjugate as a nanomicellar carrier for delivery of paclitaxel. Bioconjugate Chem. 24, 464-472 (2013).
Zhang, P., et al. Design and evaluation of a PEGylated lipopeptide equipped with drug-interactive motifs as an improved drug carrier. AAPS J. 16, 114-124 (2014).
Marciano, D. et al., Famesyl derivatives of rigid carboxylic acids-inhibitors of ras-dependent cell growth. J. Med. Chem. 38, 1267-72 (1995).
Xiong, X. B.et al., Enhanced intracellular delivery and improved antitumor efficacy of doxorubicin by sterically stabilized liposomes modified with a synthetic RGD mimetic. J. Control. Release, 107, 262-75 (2005).
Lu, J. et al. PEG-derivatized embelin as a nanomicellar carrier for delivery of paclitaxel to breast and prostate cancers. Biomaterials, 34, 1591-600 (2013).
Xiao, K. et al. A self-assembling nanoparticle for paclitaxel delivery in ovarian cancer, Biomaterials, 2009. vol. 30, pp. 6006-6016.
Gao, X. et al. Nanoassembly of surfactants with interfacial drug-interactive motifs as tailor-designed drug carriers, Molecular Pharmaceutics, Dec. 17, 2012 (E-pub) vol. 10, pp. 187-198.
A.B. Kunnumakkara, P. Anand, B.B. Aggarwal, Curcumin inhibits proliferation, invasion, angiogenesis and metastasis of different cancers through interaction with multiple cell signaling proteins, Cancer letters, 269 (2008) 199-225.
L.R. Chaudhary, K.A. Hruska, Inhibition of cell survival signal protein kinase B/Akt by curcumin in human prostate cancer cells, J Cell Biochem, 89 (2003) 1-5.
S. Lev-Ari, L. Strier, D. Kazanov, L. Madar-Shapiro, H. Dvory-Sobol, I. Pinchuk, B. Marian, D. Lichtenberg, N. Arber, Celecoxib and curcumin synergistically inhibit the growth of colorectal cancer cells, Clinical cancer research : an official journal of the American Association for Cancer Research, 11 (2005) 6738-6744.
M. Notarbartolo, P. Poma, D. Perri, L. Dusonchet, M. Cervello, N. D'Alessandro, Antitumor effects of curcumin, alone or in combination with cisplatin or doxorubicin, on human hepatic cancer cells. Analysis of their possible relationship to changes in NF-kB activation levels and in IAP gene expression, Cancer letters, 224 (2005) 53-65.
B. Rotblat, M. Ehrlich, R. Haklai, Y. Kloog, The Ras inhibitor farnesylthiosalicylic acid (Salirasib) disrupts the spatiotemporal localization of active Ras: A potential treatment for cancer, Method Enzymol, 439 (2008) 467-489.
M. Marom, R. Haklai, G. Benbaruch, D. Marciano, Y. Egozi, Y. Kloog, Selective-Inhibition of Ras-Dependent Cell-Growth by Farnesylthiosalicylic Acid, Journal of Biological Chemistry, 270 (1995) 22263-22270.
Y. Kloog, A.D. Cox, RAS inhibitors: potential for cancer therapeutics, Molecular medicine today, 6 (2000) 398-402.
R. Blum, Y. Kloog, Tailoring Ras-pathway—inhibitor combinations for cancer therapy, Drug resistance updates : reviews and commentaries in antimicrobial and anticancer chemotherapy, 8 (2005) 369-380.
J. Min, A. Zaslavsky, G. Fedele, S.K. McLaughlin, E.E. Reczek, T. De Raedt, I. Guney, D.E. Strochlic, L.E. Macconaill, R. Beroukhim, R.T. Bronson, S. Ryeom, W.C. Hahn, M. Loda, K. Cichowski, An oncogene-tumor suppressor cascade drives metastatic prostate cancer by coordinately activating Ras and nuclear factor-kappaB, Nature medicine, 16 (2010) 286-294.
M. Gana-Weisz, J. Halaschek-Wiener, B. Jansen, G. Elad, R. Haklai, Y. Kloog, The Ras inhibitor S-trans, trans-farnesylthiosalicylic acid chemosensitizes human tumor cells without causing resistance, Clinical Cancer Research, 8 (2002) 555-565.
Y. Kloog, A.D. Cox, M. Sinensky, Concepts in Ras-directed therapy, Expert opinion on investigational drugs, 8 (1999) 2121-2140.
R. Haklai, G. Elad-Sfadia, Y. Egozi, Y. Kloog, Orally administered FTS (salirasib) inhibits human pancreatic tumor growth in nude mice, Cancer chemotherapy and pharmacology, 61 (2008) 89-96.
A. Biran, M. Brownstein, R. Haklai, Y. Kloog, Down regulation of survivin and aurora A by histone deacetylase and RAS inhibitors: a new drug combination for cancer therapy, International journal of cancer. Journal international du cancer, 128 (2011) 691-701.
L. Mologni, S. Brussolo, M. Ceccon, C. Gambacorti-Passerini, Synergistic effects of combined Wnt/KRAS inhibition in colorectal cancer cells, PloS one, 7 (2012) e51449.
P. Anand, A.B. Kunnumakkara, R.A. Newman, B.B. Aggarwal, Bioavailability of curcumin: problems and promises, Molecular pharmaceutics, 4 (2007) 807-818.
A. Kraitzer, Y. Kloog, R. Haklai, M. Zilberman, Composite fiber structures with antiproliferative agents exhibit advantageous drug delivery and cell growth inhibition in vitro, Journal of pharmaceutical sciences, 100 (2011) 133-149.
Y.X. Huang, J.Q. Lu, X. Gao, J. Li, W.C. Zhao, M. Sun, D.B. Stolz, R. Venkataramanan, L.C. Rohan, S. Li, PEG-Derivatized Embelin as a Dual Functional Carrier for the Delivery of Paclitaxel, Bioconjugate Chem, 23 (2012) 1443-1451.
X. Gao, L. Huang, Potentiation of cationic liposome-mediated gene delivery by polycations, Biochemistry, 35 (1996) 1027-1036.
C. Ramachandran, H.B. Fonseca, P. Jhabvala, E.A. Escalon, S.J. Melnick, Curcumin inhibits telomerase activity through human telomerase reverse transcritpase in MCF-7 breast cancer cell line, Cancer letters, 184 (2002) 1-6.
R.A. McPherson, M.C. Conaway, C.W. Gregory, W. Yue, R.J. Santen, The novel ras antagonist, farnesylthiosalicylate, suppresses growth of prostate cancer in vitro, Prostate, 58 (2004) 325-334.
P. Starkel, N. Charette, I. Borbath, T. Schneider-Merck, C. De Saeger, J. Abarca, I. Leclercq, Y. Horsmans, Ras inhibition in hepatocarcinoma by S-trans-trans-farnesylthiosalicyclic acid: association of its tumor preventive effect with cell proliferation, cell cycle events, and angiogenesis, Molecular carcinogenesis, 51 (2012) 816-825.
K.S. Smalley, T.G. Eisen, Famesyl thiosalicylic acid inhibits the growth of melanoma cells through a combination of cytostatic and pro-apoptotic effects, International journal of cancer. Journal international du cancer, 98 (2002) 514-522.
H. Aoki, Y. Takada, S. Kondo, R. Sawaya, B.B. Aggarwal, Y. Kondo, Evidence that curcumin suppresses he growth of malignant gliomas in vitro and in vivo through induction of autophagy: role of Akt and extracellular signal-regulated kinase signaling pathways, Molecular pharmacology, 72 (2007) 29-39.
L. Li, F.S. Braiteh, R. Kurzrock, Liposome-encapsulated curcumin: in vitro and in vivo effects on proliferation, apoptosis, signaling, and angiogenesis, Cancer, 104 (2005) 1322-1331.
M.M. Yallapu, M. Jaggi, S.C. Chauhan, Curcumin nanoformulations: a future nanomedicine for cancer, Drug discovery today, 17 (2012) 71-80.
L. Liu, L. Sun, Q.J. Wu, W.H. Guo, L. Li, Y.S. Chen, Y.C. Li, C.Y. Gong, Z.Y. Qian, Y.Q. Wei, Curcumin loaded polymeric micelles inhibit breast tumor growth and spontaneous pulmonary metastasis, Int J Pharmaceut, 443 (2013) 175-182.
H. Maeda, J. Wu, T. Sawa, Y. Matsumura, K. Hori, Tumor vascular permeability and the EPR effect in macromolecular therapeutics: a review, J Control Release, 65 (2000) 271-284.
H. Cabral, Y. Matsumoto, K. Mizuno, Q. Chen, M. Murakami, M. Kimura, Y. Terada, M.R. Kano, K. Miyazono, M. Uesaka, N. Nishiyama, K. Kataoka, Accumulation of sub-100 nm polymeric micelles in poorly permeable tumours depends on size, Nat Nanotechnol, 6 (2011) 815-823.

* cited by examiner

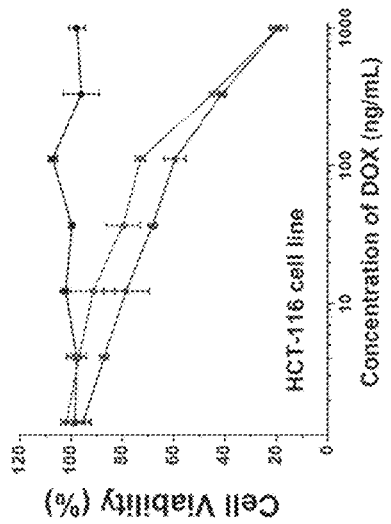
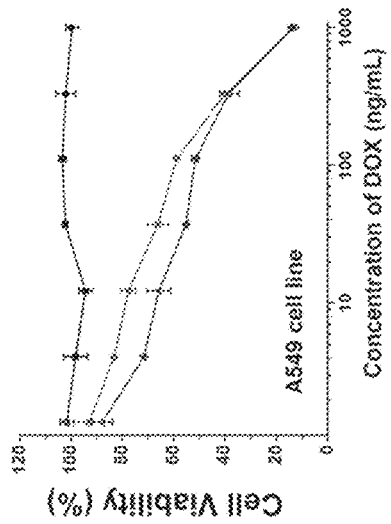
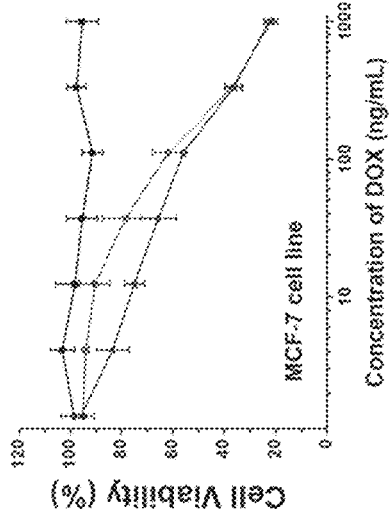
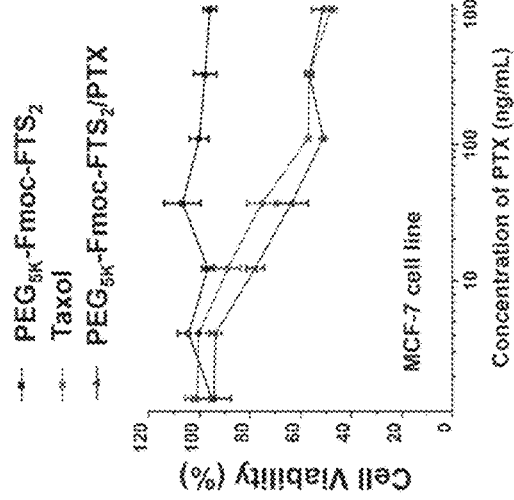
Fig. 13A  Fig. 13B  Fig. 13C  Fig. 13D  Fig. 13E  Fig. 13F

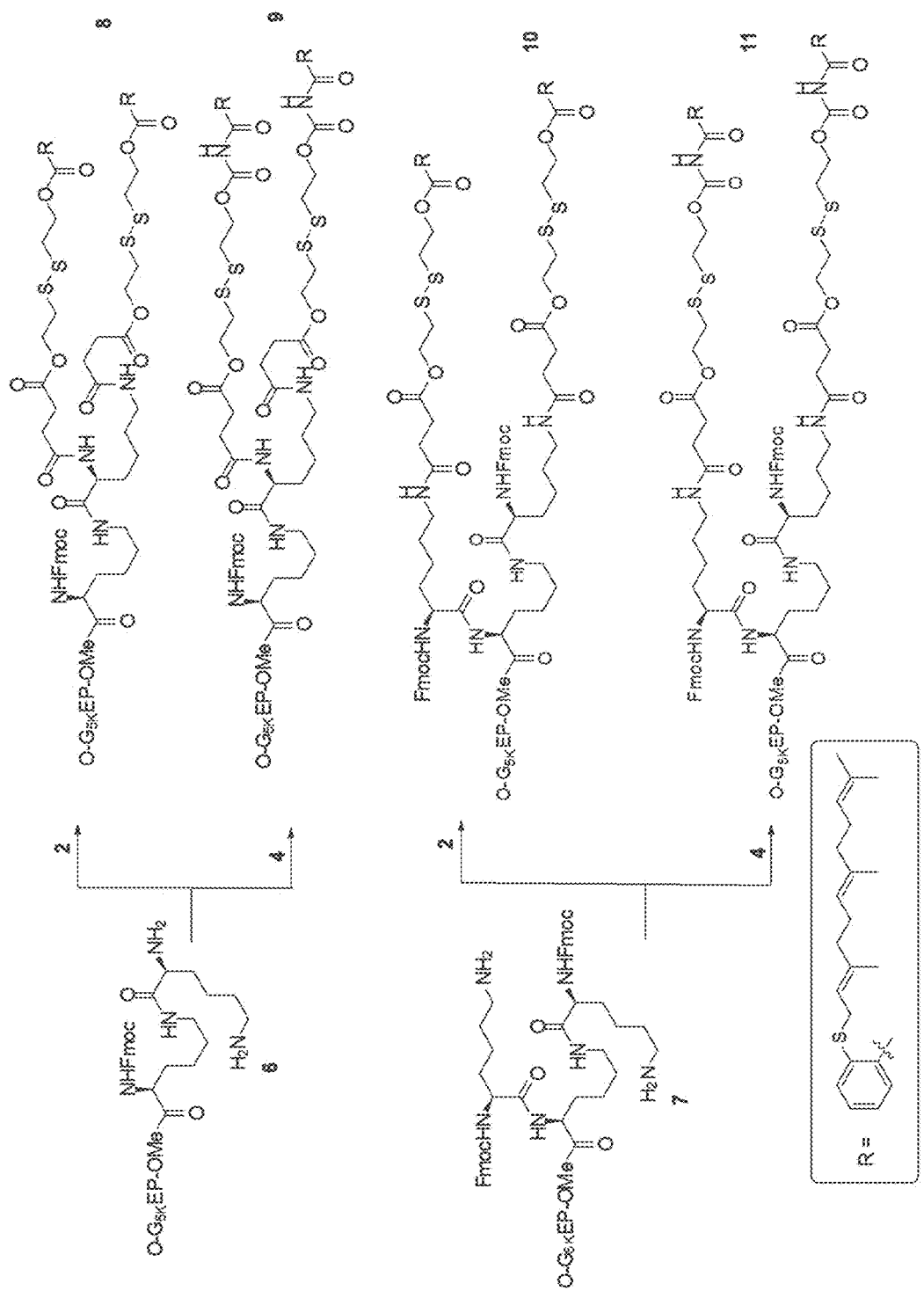
Fig. 17A(ii)

FORMULATIONS AND CARRIER SYSTEMS INCLUDING FARNESYLTHIOSALYCYLIC MOITIES

CROSS-REFERENCE TO RELATED APPLICATIONS

This application claims benefit of U.S. Provisional Patent Application Ser. No. 61/941,998, filed Feb. 19, 2014, the disclosure of which is incorporated herein by reference.

GOVERNMENTAL INTEREST

This invention was made with government support under grant nos. R01GM102989, and R21CA155983 awarded by the National Institutes of Health. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Poor water solubility is one of the major hurdles for the advancement of drug candidates into clinical applications. Most drug companies focus on orally deliverable drugs. Not all drugs are orally bioavailable, however. Bioavailability may, for example, be defined as the fraction of an administered dose of unchanged drug that reaches, for example, the systemic circulation. Some compounds/drugs may be degraded in the digest tract, while some may be too harmful for the epithelial lining. In many cases, the duration of the free drug in blood once absorbed is very short. Any one or combination of these problems for a drug candidate may result in the elimination or cessation of drug development (as a general practice in the pharmaceutical industry).

The current drug discovery process is costly and inefficient. Many promising drug candidates have failed to reach the market primarily as a result of poor water solubility, low bioavailability and toxicity issues. Formulation development thus represents an important strategy to maximize the success of drug discovery. In addition, formulations can improve the therapeutic index of existing drugs. Among various types of delivery systems studied, polymeric micelles have gained considerable attention due to their simplicity, small sizes (10-100 nm), and the ability to solubilize water-insoluble drugs and accumulate specifically at the tumors. Most of the carrier materials in polymeric drug delivery systems (including lipid-core micellar systems) utilize "inert" excipients that lack therapeutic effect. The use of excess amounts of carrier materials may, for example, add to cost and potentially impose safety issues.

SUMMARY

In one aspect, a method of forming or creating a formulation for a compound to be delivered includes creating a carrier agent by conjugating at least one hydrophobic domain or hydrophobic compound with at least one hydrophilic domain or hydrophilic compound and associating the compound to be delivered with the carrier agent to create the formulation. The at least one hydrophobic compound has the formula:

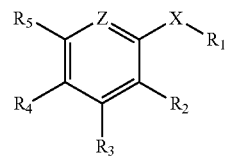

wherein $R_1$ is a farnesyl group, a geranyl group or geranylgeranyl group, X is O, S, SO, $SO_2$, NH or Se, Z is C—$R_2$ or N, $R_2$ is H, CN, $CO_2R_7$, $SO_3R_7$, $CONR_7R_8$ or $SO_2NR_7R_8$, wherein $R_7$ and $R_8$ are each independently H, an alkyl group, an alkenyl group, $CO_2M$ or $SO_3M$, wherein M is a cation and $R_3$, $R_4$, and $R_5$ are independently H, a carboxyl group, an alkyl group, an alkenyl group, an aminoalkyl group, a nitroalkyl group, a nitro group, a halo atom, an amino group, a mono-alkylamino group, a di-alkylamino group, mercapto group, a mercaptoalkyl group, an azido group or a thiocyanato group. In general, M is a metal cation such as $K^+$, $Na^+$, $Li^+$, $Rb^+$, $Cs^+$, $Ag^+$ etc.). A ferensyl group has the following formula:

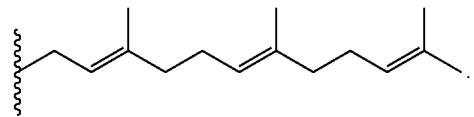 [SMILES: *C/C=C(\C)CC/C=C(\C)CCC=C(C)C ; "."]

A garnyl group has the following formula:

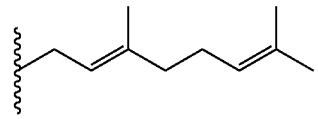

A garnylgarnly group has the following formula:

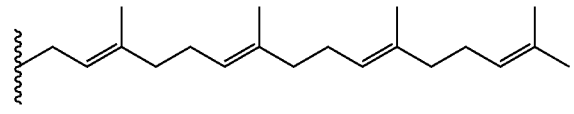

The term "alkyl" and other groups refer generally to both unsubstituted and substituted groups unless specified to the contrary. Unless otherwise specified, alkyl groups are hydrocarbon groups and are $C_1$-$C_{15}$ (that is, having 1 to 15 carbon atoms) alkyl groups or $C_1$-$C_{10}$ alkyl groups, and can be branched or unbranched, acyclic or cyclic. The above definition of an alkyl group and other definitions apply also when the group is a substituent on another group (for example, an alkyl group as a substituent of an alkylamino group or a dialkylamino group). The term "alkenyl" refers to a straight or branched chain hydrocarbon group with at least one double bond, with 2-15 carbon atoms or with 2-10 carbon atoms. As used herein, the terms "halogen" or "halo" refer to fluoro, chloro, bromo and iodo.

In a number of embodiments, a plurality of the carrier agents are adapted to assemble into a structure. Such a structure may, for example, be a micelle, a cream, a liposome, a spherulite, a solid-lipid nanoparticle, a hydrogel, a cubic phase lipogels or other others. In a number of embodiments, a plurality of the carrier agents are adapted to self-assemble into a micelle. Micelles may, for example, have an average size less than 100 nm, less than 50 nm, less than 40 nm or less than 35 nm. The compound to be delivered may, for example, be incorporated within the micelle. In a number of embodiments the compound to be delivered, which is associated with the carrier agent, is a biologically active compound.

One or more hydrophilic compound may, for example, be conjugated to the biologically active hydrophobic compound at, for example, any one or more of $R_2$, $R_3$, $R_4$ or $R_5$. In a number of embodiments, the hydrophobic compound is cleavably conjugated (for example, via a cleavable covalent bond) to the at least one hydrophilic compound via a linkage which is labile in vivo. The hydrophobic compound or an analog thereof may thus be released from the carrier agent under physiological conditions. In a number of embodiments, the cleavable linkage includes at least one of an ester linkage, a disulfide linkage, a pH-sensitive linkage, a ROS-sensitive linkage, or a protease-sensitive linkage. In a number of embodiments, the cleavable linkage includes at least one disulfide linkage.

The at least one hydrophobic compound may, for example, be selected from the group consisting of farnesylthiosalicylic acid and a biologically active derivative of farnesylthiosalicylic acid such that a biologically active from of the hydrophobic compound is released in vivo. In a number of embodiments, the hydrophobic compound is selected from the groups consisting of S-trans, trans-farnesylthiosalicylic acid and other biologically active derivatives or analogs of farnesylthiosalicylic acid. The biologically active derivative of farnesylthiosalicylic acid may, for example, be S-trans, trans-farnesylthiosalicylic acid, S-trans, trans-farnesylthiosalicylic acid amide, S-trans, trans-farnesylthiosalicylic acid methylamide (FTS-MA) or S-trans, trans-farnesylthiosalicylic acid dimethylamide (FTS-DMA). Other biologically active farnesylthiosalicylic acid derivatives are also suitable for user herein.

A biologically active compound to be delivered via the carrier agent may, for example, be a drug. The biologically active compound may, for example, include or be an amphetamine, a steroid, an anesthetic, an analgesic, an antacid, an antibiotic, an anticoagulant, an antidepressant, an antidote, an antihistamine, an anti-inflammatory, an antimycotic, an anticancer agent, an analgesic agent, an antirejection agent, an antiretroviral, an antiviral, a barbiturate, a beta blocker, a booster, a contraceptive, a decongestant, a depressant, an emetic, an expectorant, a hypnotic, an immunosuppressant, a laxative, a narcotic, a neurochemical, an opiates, a painkiller, a prophylactic, a purgative, a relaxant, a sedative, a statin, a suppressant, a tranquilizer, a vaccine, a vitamin or a prodrug thereof. In a number of embodiments, the biologically active compound is or includes an anti-inflammatory agent or an anticancer agent. Representative biologically active compounds/drugs include, but are not limited to, paclitaxel (PTX), curcumin, tamoxifen, doxorubicin (DOX), bicalutamide, etoposide, camptothecin, pemetrexed, docetaxel, epirubicin, doxorubicin, vinblastine, vindesine, etoposide, hydroxycamptothecin, irinotecan, mitoxantrone, tamoxifen, imatinib, gefitinib, erlotinib, sorafenib, bortezomib or an analog of any such drug.

The at least one hydrophilic compound may, for example, include at least one hydrophilic oligomer or at least one hydrophilic polymer. The at least one hydrophilic oligomer or the at least one hydrophilic polymer may, for example, be selected from the group consisting of a polyalkylene oxide, a polyvinylalcohol, a polyacrylic acid, a polyacrylamide, a polyoxazoline, a polysaccharide and a polypeptide. In a number of embodiments, the polyalkylene oxide is a polyethylene glycol.

In a number of embodiments, the carrier agent is created by conjugating the at least one hydrophobic compound/domain with at least one compound interactive agent and the at least one hydrophilic compound. The at least one compound interactive agent includes at least one group that interacts with the compound to be delivered. The at least one compound interactive agent may be positioned such that it is intermediate between the hydrophobic compound/domain and the at least one hydrophilic compound/domain in the carrier agent. In that regard, the at least one interactive agent is positioned to be in the vicinity of the interface between the hydrophobic domain and the hydrophilic domain in the structure (for example, micelles) formed by the carrier agents. In a number of embodiments, the at least one compound interactive agent includes at least one of a fluorenylmethyloxycarbonyl group, a carbobenzyloxy group, an isobutoxycarbamate group, a naphthylacetyl group, a carbazole group, a quinolone group, an isoquinolone group, or a group which is a residue of a molecule selected from the group of the compound, a portion of the compound, (9H-fluoren-9-yl)methanamine, (9H-fluoren-9-yl)methanol, 9H-fluoren-9-amine, naphthalene, 1,1'-bi-2-naphthol (BINOL), camptothecin, a camptothecin analog, pemetrexed, docetaxel, paclitaxel, epirubicin, doxorubicin, vinblastine, vindesine, etoposide, hydroxycamptothecin, irinotecan, mitoxantrone, tamoxifen, curcumin, imatinib, gefitinib, erlotinib, sorafenib, and bortezomib, (add NLG?) or a derivative thereof. In a number of embodiments, the at least one compound interactive agent includes at least one fluorenylmethyloxycarbonyl group or a derivative thereof.

In another aspect, a formulation to deliver a compound (for example, a biologically active compound) to a patient includes the compound to be delivered and a carrier agent as described above. In that regard, a method of delivering a biologically active compound to a patient may, for example, include delivering to the patient a composition comprising a carrier agent formed by conjugating at least one biologically active hydrophobic compound with at least one hydrophilic compound, the at least one biologically active hydrophobic compound having the formula:

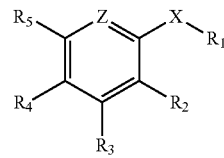

wherein $R_1$ is a farnesyl group, a geranyl group or geranylgeranyl group, X is O, S, SO, $SO_2$, NH or Se, Z is C—$R_2$ or N, $R_2$ is H, CN, $CO_2R_7$, $SO_3R_7$, $CONR_7R_8$ or $SO_2NR_7R_8$, wherein $R_7$ and $R_8$ are each independently H, an alkyl group, an alkenyl group, $CO_2M$ or $SO_3M$, wherein M is a cation and $R_3$, $R_4$, and $R_5$ are independently H, a carboxyl group, an alkyl group, an alkenyl group, an aminoalkyl group, a nitroalkyl group, a nitro group, a halo atom, an amino group, a mono-alkylamino group, a di-alkylamino group, mercapto group, a mercaptoalkyl group, an azido group or a thiocyanato group, wherein a plurality of the carrier agents are adapted to assemble into a structure and the at least one biologically active hydrophobic compound is conjugated with the at least one hydrophilic compound via a linkage which is labile in vivo. The composition further includes the biologically active compound associated with the carrier agent.

In another aspect, a composition is formed by conjugating at least one hydrophobic domain or compound with at least one hydrophilic domain or compound as described above. In a number of embodiments, the hydrophobic compound is selected from the group consisting of farnesylthiosalicylic acid and a biologically active derivative of farnesylthiosalicylic. Such compositions may, for example, be used as carrier agents as described above or as a delivery agent for a biologically active hydrophobic compound such as farnesylthiosalicylic acid or a biologically active derivative of farnesylthiosalicylic acid.

In a further aspect, a method of delivering a compound to a patient includes delivering to the patient a formulation or composition as described above.

In still a further aspect, a method of treating a patient includes administering a pharmaceutically effective amount of the compound to be delivered (for example, a drug or a pharmaceutically acceptable salt thereof) via the composition or formulation described above. The method may also include administering a pharmaceutically effective amount of the biologically active hydrophobic compound via the composition or formulation. The compositions or formulations may be administered by any conventional route of administration, including, but not limited to, intravenously, intramuscularly, orally, subcutaneously, intratumorally, intradermally, and parenterally. In general, a pharmaceutically effective amount or dosage is predetermined or determinable as known in the medical arts. Patients may, for example, be treated for any type of disease for which the compound to be delivered is pharmaceutically effective. The biologically active hydrophobic compounds hereof may, for example, provide further or synergistic pharmaceutical effect as a RAS antagonist or as an anti-inflammatory.

As described above, the at least one hydrophilic compound of the hydrophilic domain(s) of the carrier agents hereof may, for example, include at least one hydrophilic oligomer or at least one hydrophilic polymer. The term "polymer" refers generally to a molecule of high relative molecular mass, the structure of which includes repeat units derived, actually or conceptually, from molecules of low relative molecular mass (monomers). The term "oligomer" refers generally to a molecule of intermediate relative molecular mass, the structure of which includes a small plurality of units derived, actually or conceptually, from molecules of lower relative molecular mass (monomers). In general, a polymer is a compound having >1, and more typically >10 repeat units or monomer units, while an oligomer is a compound having >1 and <20, and more typically <10 repeat units or monomer units. In a number of embodiments, the hydrophilic oligomer or the hydrophilic polymer is a polyalkylene oxide, a polyvinylalcohol, a polyacrylic acid, a polyacrylamide, a polyoxazoline, a polysaccharide or a polypeptide. In a number of embodiments, the polyalkylene oxide is a polyethylene glycol. The hydrophilic compound(s) which form the hydrophilic domain(s) hereof may, for example, include at least one ionic group. In a number of embodiments, the at least one hydrophilic compound(s) include at least one carboxylic acid group, at least one amine group, at least one saccharide group, or at least one polysaccharide group.

In a number of embodiments, the hydrophilic compound (for example, PEG) has a molecular weight of at least 1 KDa (for example, in the range of approximately 1 KDa to 10 KDa). In a number of embodiments, the hydrophilic domain has a molecular weight in the range of approximately 1 KDa to 5 KDa. The at least one compound interactive agent may, for example, have a molecular weight in the range of approximately 300 Da to 2 KDa. The hydrophilic, hydrophobic and intermediate drug-interactive domains of the carrier agent may, for example, include a single or multiple chains.

Once again, the compositions, carrier agents and formulations hereof may, for example, form (or self-assemble into) a structure or complex such as, for example, a micelle, an emulsion, a cream, a liposome, a spherulite, a solid-lipid nanoparticle, a hydrogel or a cubic phase lipogel. As described above, in a number of embodiments, the compound with which the carrier agent interacts is a biologically active compound or a drug. A drug is a biologically active substance which has an effect on the body (for example, a medicinal or therapeutic effect, an intoxicating effect, a performance enhancing effect or another effect).

The carrier agents hereof may, for example, provide a compound to be delivered/drug loading capacity of at least 10%, at least 20%, at least 30% or even at least 40%. In general, the loading capacity of the carrier agent may, for example, be increased via inclusion of a compound interactive domain or agent as described above. Likewise, the stability may also be increased. For example, an amphiphilic carrier agent hereof may have a greater loading capacity than an amphiphilic molecule including only the hydrophobic compound(s)/domain and the hydrophilic compound(s)/domain of the amphiphilic carrier system hereof.

In a number of embodiments, the interfacial region of an amphiphilic carrier agent/molecule hereof is modified (for example, enlarged and/or expanded) by inserting a compound/drug interactive agent or segment (for example, including an amino acid or a peptide segment). Additionally, pendant groups on the amino acid or other residues may be incorporated that exhibit drug-interactive potential. The at least one group of the compound/drug interactive agent, segment or domain that interacts with the compound may, for example, have an affinity for the compound. The compound to be delivered may thus associate with the carrier agent without being bonded thereto. Compound/drug interactive agents, domains or segments hereof may, for example, be capable of π-π hydrophobic/aromatic ring stacking or hydrogen-bonding interactions to enhance the carrier-compound/drug interaction as a way to stabilize drug formulation.

In a number of embodiments, the at least one compound interactive agent/domain of the carrier agent is covalently bonded to the at least one hydrophilic domain. In a number of embodiments, the at least one compound interactive agent of carrier agent is covalently bonded (directly or indirectly—for example, via a linker) to the at least one hydrophilic domain and/or is covalently bonded (directly or indirectly—for example, via a linker) to the at least one hydrophobic domain. As described above, in a number of embodiments, the biologically hydrophobic compound or a biologically active analog or derivative thereof 9 of the hydrophobic domain of a carrier agent hereof) is cleavable from the remainder of the carrier agent under physiological conditions.

The present agents, systems, methods, formulations and compositions, along with the attributes and attendant advantages thereof, will best be appreciated and understood in view of the following detailed description taken in conjunction with the accompanying drawings.

BRIEF DESCRIPTION OF THE DRAWINGS

FIG. 13A illustrates a study of anticancer/antitumor effect of TAXOL, drug-free, and PTX-loaded PEG5k-Fmoc-FTS$_2$ micelles on a MCF-7 human breast carcinoma cell line.

FIG. 13B illustrates a study of anticancer effect of TAXOL, drug-free, and PTX-loaded PEG5k-Fmoc-FTS$_2$ micelles on a A549 human lung adenocarcinoma epithelial cell line.

FIG. 13C illustrates a study of anticancer effect of TAXOL, drug-free, and PTX-loaded PEG5k-Fmoc-FTS$_2$ micelles on a HCT-116 human colon carcinoma cell line.

FIG. 13D illustrates a study of anticancer/antitumor effect of free DOX, drug-free, and DOX-loaded PEG5k-Fmoc-FTS$_2$ micelles on a MCF-7 human breast carcinoma cell line.

FIG. 13E illustrates a study of anticancer/antitumor effect of free DOX, drug-free, and DOX-loaded PEG5k-Fmoc-FTS$_2$ micelles on an A549 human lung adenocarcinoma epithelial cell line.

FIG. 13F illustrates a study of anticancer effect of DOX, drug-free, and DOX-loaded PEG5k-Fmoc-FTS$_2$ micelles on a HCT-116 human colon carcinoma cell line, wherein cells were treated for 72 h, cytotoxicity was determined by MTT assay, and values reported are the means±SD for triplicate samples in each of FIGS. 13A through 13F.

FIG. 17A(ii) illustrates further embodiments of schemes for the synthesis of various Fmoc-containing PEG-FTS (FTS-amide) conjugates.

DESCRIPTION

Figure 1:
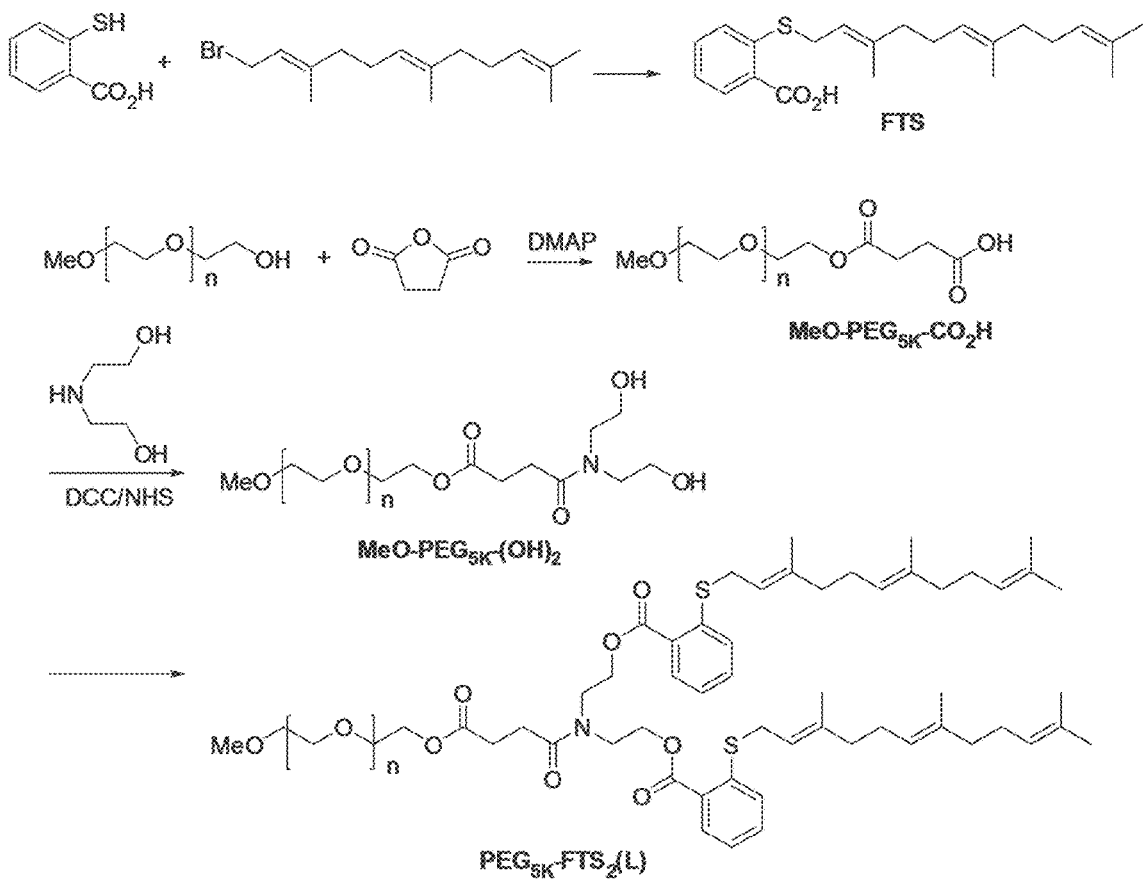
FIG. 1 illustrates an embodiment of a synthetic scheme for the synthesis of PEG$_{5K}$-FTS$_2$(L) wherein the FTS segments are attached to PEG via a labile ester linkage.
Figure 2:
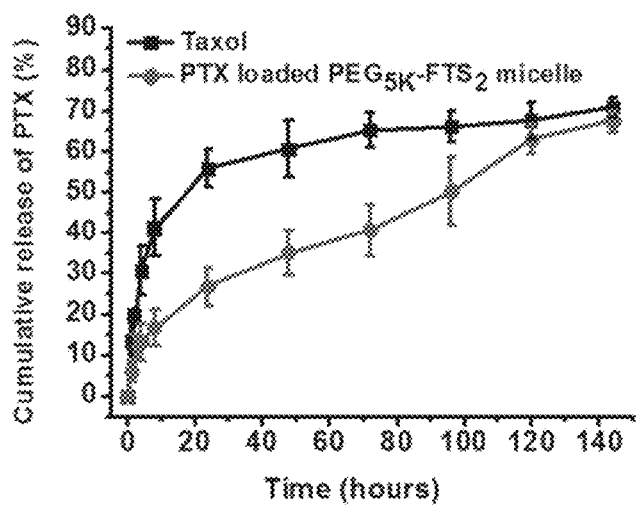
FIG. 2 illustrates a cumulative paclitaxel (PTX) release profile from TAXOL® (paclitaxel or PTX) and PEG$_{5K}$-FTS$_2$ micelles.

It will be readily understood that the components of the embodiments, as generally described herein and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a compound" includes a plurality of such compounds and equivalents thereof known to those skilled in the art, and so forth, and reference to "the compound" is a reference to one or more such compound and equivalents thereof known to those skilled in the art, and so forth. Recitation of ranges of values herein are merely intended to serve as a shorthand method of referring individually to each separate value falling within the range. Unless otherwise indicated herein, and each separate value as well as intermediate ranges are incorporated into the specification as if it were individually recited herein. All methods described herein can be performed in any suitable order unless otherwise indicated herein or otherwise clearly contraindicated by the text.

Through drug-carrier agent interaction and time-dependent dispersion processes, a regulated drug release can be achieved from drug-carrier agent dosing regimens in the forms of, for example, granules, pellets and other physical forms. Although carrier agents hereof are discussed primarily in connection with representative examples of drugs, the carrier agents hereof are suitable for use in connection with other compounds or molecules.

An approach in the design of a carrier agent or system is that components of the carrier agent or system exhibit biological activity (for example, counteracting the side effects caused by the loaded drugs, or promoting synergistic effect with the incorporated drugs). S-trans, trans-farnesylthiosalicylic acid (FTS), which is shown below,

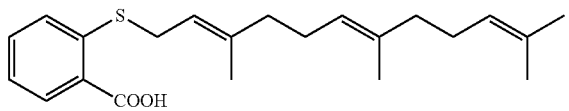 [SMILES: CC(C)=CCC/C(C)=C/CC/C(C)=C/CSc1ccccc1C(=O)O]

is a synthetic farnesylcysteine mimetic that acts as a potent and especially nontoxic Ras antagonist. Constitutively active Ras caused by mutation in the Ras family of proto-oncogenes is present in one-third of human cancers, with the highest incidence of mutational activation of Ras being detected in pancreatic (90%) and colon (50%) cancers. Ras is also activated in cancer cells by other mechanisms. In particular, hyperactivation of the epidermal growth factor receptor (EGFR) tyrosine kinase activity causes persistent activation of Ras and Ras-mediated signaling. The activated form of Ras constitutively activates its downstream effectors, contributing to cell transformation. FTS can inhibit both oncogenically activated Ras and growth factor receptor-mediated Ras activation, resulting in the inhibition of Ras-dependent tumor growth. FTS can inhibit Ras transforming activity and reverse the transformed phenotype of Ras-transformed fibroblasts. FTS has demonstrated significant reduction of Ras levels in a wide array of established cancer models and inhibition of tumor growth in animals with no adverse toxicity. One major mechanism involves affecting membrane interaction of Ras by competing with Ras for binding to Ras-escort proteins, facilitating its degradation, and thus disrupting Ras protein to signal in the plasma membrane. In addition to its antitumor activity, FTS also exhibits anti-inflammatory activity.

FTS has a hydrophobic nature and limited oral bioavailability. Conjugation of FTS or another hydrophobic, bioactive agent having the formula:

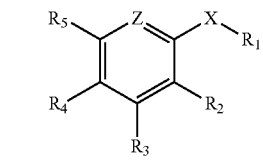

Wherein $R_1$, $R_2$, $R_3$, $R_4$, $R_5$, X and Z are defined as describe above with one or more hydrophilic compounds (for example, hydrophilic oligomers or polymers such a polyethylene glycol or PEG) as described herein improves the solubility of the hydrophobic compound. The compounds of the above formula are, for example, biologically active as RAS antagonists and may also exhibit anti-inflammatory bioactivity. A biological active hydrophobic compound such as FTS may be retained in a conjugate with a labile linkage (for example, an ester linkage and/or a disulfide linkage). In contrast, a conjugate with a relatively stable (non-labile or non-cleavable) linkage, may be significantly less active. Although, a conjugate with a stable linkage may be used as a carrier agent (for example, for drug delivery), a bioactive hydrophobic conjugate with a labile linkage may, for example, provide additional and/or synergistic biological activity.

We found that representative FTS conjugates with hydrophilic compounds such a PEG forms small-sized micelles (for example, in the range of 20-30 nm in a number of embodiments PEG-FTS conjugates) that are highly efficient in solubilizing other compounds/drugs including, but not limited to, paclitaxel (PTX), doxorubicin (DOX), and curcumin. In a number of representative studies, delivery of PTX via $PEG_{5K}$-$FTS_2(L)$ (wherein L designates a labile or cleavable covalent linkage between $PEG_{5k}$ and FTS) micelles led to synergistic antitumor activity both in vitro and in vivo, more effective than PTX formulated in $PEG_{5K}$-$FTS_2(S)$ (wherein S designates a stable or non-labile covalent linkage between $PEG_{5k}$ and FTS) micelles. The data indicated that PEG-FTS conjugates perform as a dual functional carrier, and that the cleavability of the linkage between PEG and FTS affects the overall antitumor activity of drug/PEG-FTS mixed micelles.

To facilitate retention of the biological activity of FTS (or another biologically active hydrophobic compound as describe herein), many types of labile or cleavable linkages may be used to connect FTS to one or more hydrophilic compounds in a number of embodiments hereof. For example, FTS may be linked with a hydrophilic compound such as PEG via a cleavable ester linkage or disulfide linkage.

FIG. 1 illustrates the synthesis of a $PEG_{5K}$-$FTS_2(L)$ (once again, wherein "L" denotes a labile linkage of the FTS) conjugate with a labile ester linkage via solution phase condensation reactions from MeO-PEG-OH with a molecular weight of 5000. We also synthesized $PEG_{5K}$-$FTS_2(S)$ (once again, wherein "S" denotes a stable linkage of the FTS) conjugate in which FTS was coupled onto PEG chain via a stable amide linkage. The $PEG_{5K}$-$FTS_2$ conjugate readily formed micelles in aqueous solution. Dynamic light scattering (DLS) measurements showed that these micelles had hydrodynamic sizes around 22 nm at the concentration of 20 mg/mL. Transmission electronic microscopy (TEM) revealed spherical particles with uniform size distribution. The size observed by TEM showed good agreement with that determined by DLS. PTX could be effectively loaded into $PEG_{5K}$-$FTS_2$ micelles. The size and size distribution were not significantly affected when PTX was loaded into micelles at a drug concentration of 1 mg/mL and a carrier/drug ratio of 5/1 (m/m). The critical micelle concentration (CMC) of $PEG_{5K}$-$FTS_2$ micelles was measured using pyrene as a fluorescence probe. The CMC of the $PEG_{5K}$-$FTS_2$ micelles was determined to be 0.68 µM.

Table 1 shows the sizes of PTX-loaded micelles at different carrier/drug molar ratios. All of the micelles had relatively small size of around 20 nm. With increases in the input molar ratio of $PEG_{5K}$-$FTS_2$/PTX, the sizes of the PTX-loaded micelles were closer to that of drug-free micelles. The drug loading efficiency of $PEG_{5K}$$FTS_2$ micelles was over 90% at various carrier/drug ratios examined. The drug loading efficiency was quantified by high-performance liquid chromatography (HPLC). Drug loading capacity (DLC) and drug loading efficiency (DLE) were calculated according to the following equations:

DLC(%)=[weight of drug used/(weight of polymer+ drug used)]×100%

DLE(%)(weight of loaded drug/weight of input drug)×100%

TABLE 1

| Micelle | molar ratio | conc.. of PTX[a] (mg/mL) | size[b] (nm) | PDI[c] | DLE[d] (%) | DLC[e] (%) |
|---|---|---|---|---|---|---|
| PEG5K-FTS2 | — | — | 17.61 ± 0.9 | 0.201 | — | — |
| PEG5K-FTS2:PTX | 3.75:1 | 1 | 24.93 ± 1.2 | 0.354 | 90.6 | 3.73 |
| PEG5K-FTS2:PTX | 5:1 | 1 | 25.63 ± 3.4 | 0.234 | 97.6 | 2.82 |
| PEG5K-FTS2:PTX | 7.5:1 | 1 | 22.27 ± 0.6 | 0.268 | 98.0 | 1.90 |
| PEG5K-FTS2:PTX | 10:1 | 1 | 20.17 ± 0.2 | 0.189 | 96.2 | 1.43 |

[a]PTX concentration in micelle was kept at 1 mg/mL. Blank micelle concentration was 20 mg/mL. Values reported are the mean ± SD for triplicate samples.
[b]Measured by dynamic light scattering particle sizer.
[c]PDI = polydispersity index.
[d]DLE = drug loading efficiency.
[e]DLC = drug loading capacity An advantage of the PEG-FTS micellar systems hereof is the very small size (~20 nm) of the micelles. It is generally regarded that particles in the size of 100-200 nm can be passively targeted to tumors via the leaky tumor vasculature. However, recent studies have shown that the size of the particles needs to be below 50-60 nm for them to effectively reach the poorly vascularized tumors. The small size of PEG-FTS micelles allows effective passive targeting to various types of cancers including those with poorly developed tumor vasculature.

Figure 4:
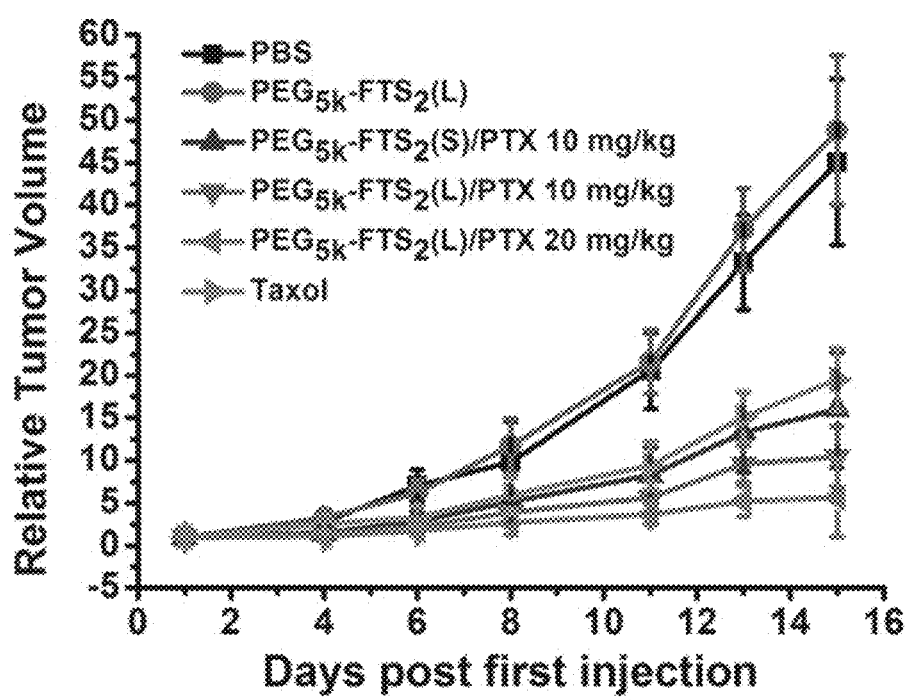
FIG. 4 illustrates a study of changes of relative tumor volume as a function of days post first injection of PTX formulated in PEG5K-FTS2(L) and PEG5K-FTS(S) micelles, wherein BABL/c mice were inoculated s.c. with 4T1.2 cells (1×105 cells/mouse) and, five days later, mice received various treatments twice a week and tumor growth was monitored and plotted as relative tumor volume (mm$^3$).

In vitro release study showed significantly slower release kinetics for PTX formulated in $PEG_{5K}$-$FTS_2$ micelles compared to Taxol formulation as illustrated in FIG. 4. Without limitation to any mechanism, this might be a result of a more effective drug/carrier interaction for PTX/$PEG_{5K}$-$FTS_2$ mixed micelles. FTS has a benzene ring and an acyl chain. In addition to hydrophobic interaction with PTX, the π-π stacking and the hydrogen bonding also contribute to the overall carrier/PTX interaction. The close proximity of two FTS molecules in $PEG_{5K}$-$FTS_2$ conjugate enhances the interaction of the carrier with PTX. Indeed, a PEG-FTS conjugate of 1:1 molar ratio was much less active than $PEG_{5K}$-$FTS_2$ in forming stable mixed micelles with PTX.

Figure 3A:
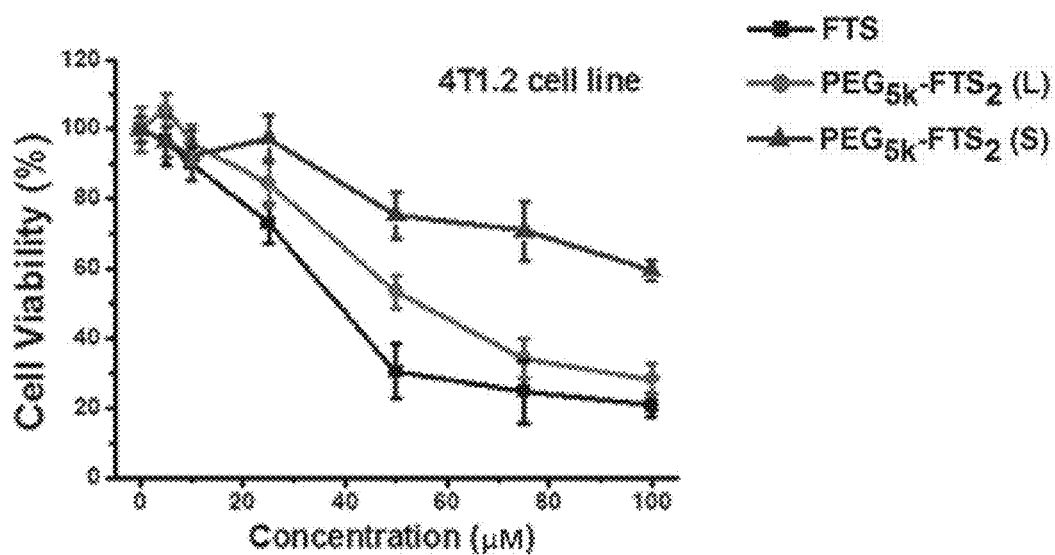
FIG. 3A illustrates a study of cytotoxicity of free FTS, PEG$_{5K}$-FTS$_2$(L), and PEG$_{5K}$-FTS$_2$(S) (wherein FTS is attached to PEG via a stable or non-labile linkage) in a 4T1.2 mouse breast cancer cell line.
Figure 3B:
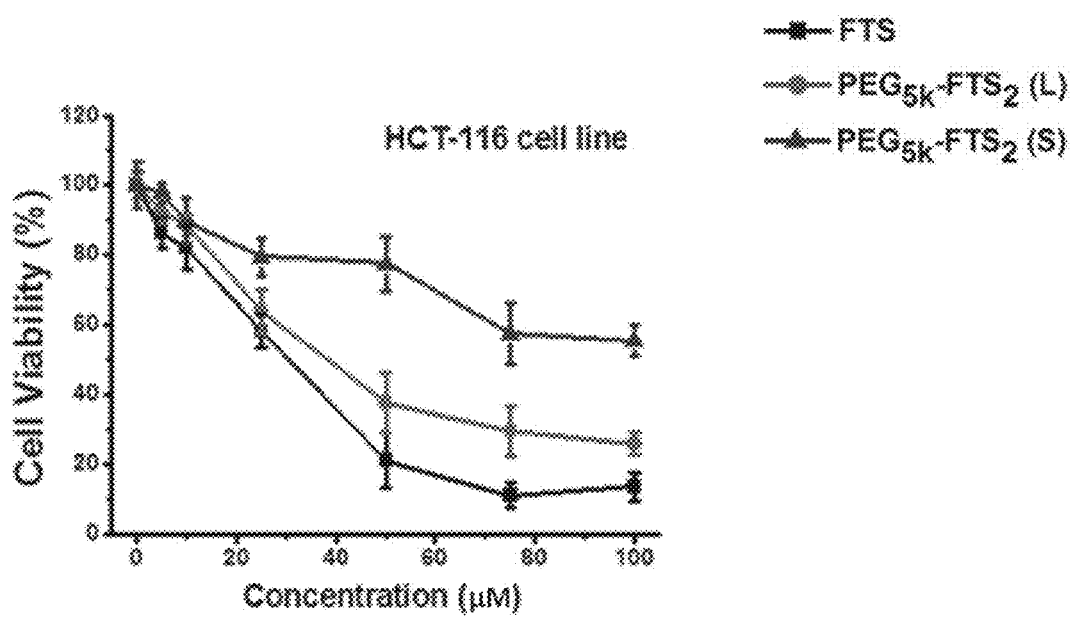
FIG. 3B illustrates a study of cytotoxicity of free FTS, PEG$_{5K}$-FTS$_2$(L), and PEG$_{5K}$-FTS$_2$(S) in a HCT-116 human colon carcinoma cell line.

Several cancer cell lines were included in the cytotoxicity studies including murine breast cancer cells 4T1.2, human colon carcinoma cell line HCT-116, and two human prostate cancer cell lines PC-3 and DU145. FIG. 3A shows the cytotoxicity of two PTX-free micelles, $PEG_{5K}$-$FTS_2(L)$ and $PEG_{5K}$-$FTS_2(S)$, in comparison with free FTS in 4T1.2 tumor cells. Free FTS inhibited the tumor cell growth in a concentration-dependent manner. Conjugation of FTS to PEG via a labile ester linkage resulted in only a slight decrease in antitumor activity as compared to FTS. In contrast, the similar conjugate with a stable amide linkage ($PEG_{5K}$-$FTS_2(S)$) was significantly less active compared to both free FTS and $PEG_{5K}$-$FTS_2$ (L). A similar result was obtained in human colon cancer cells, HCT-116 as illustrated in FIG. 3B. $PEG_{5K}$-$FTS_2(L)$ alone was thus much more active than $PEG_{5K}$-$FTS_2(S)$ in antitumor activity in both 4T1.2 (a synergistic murine breast cancer model) and HCT-116 (a human colon carcinoma) cell lines. Without limitation to any mechanism, it is unlikely that this is attributed to differences in the surface activity of the two conjugates, as both showed minimal hemolytic activity at the concentrations that were much higher than those used in the cytotoxicity study. Without limitation to any mechanism, it is likely that FTS is much more readily released from $PEG_{5K}FTS_2(L)$ by esterases following intracellular delivery. The cytotoxicity data agree with Western blotting in which PEG$_{5K}$FTS$_2$ (L) was more active than PEG$_{5K}$-FTS$_2$(S) in reducing the protein expression levels of Ras in treated tumor cells. In addition to more potent antitumor activity by itself, PEG$_{5K}$-FTS$_2$(L) was also more active than PEG$_{5K}$-FTS$_2$(S) in mediating PTX cytotoxicity to tumor cells.

Thus, conjugates of PEG with two molecules of FTS form small-sized micelles that effectively solubilize the representative drug PTX. PTX formulated in this micellar system shows a PTX release kinetics that is significantly slower than that of TAXOL. PEG$_{5K}$-FTS$_2$(L) conjugate retains the biological activity of FTS well, and PTX formulated in PEG$_{5K}$-FTS$_2$(L) micelles is more active in cytotoxicity than free PTX in vitro. In vivo, PTX/PEG$_{5K}$FTS$_2$, PEG$_{5K}$-FTS$_2$ (L) shows antitumor activity that is more potent than that of TAXOL or PTX/PEG$_{5K}$-FTS$_2$(S) (FIG. 4). PEG$_{5K}$-FTS$_2$(L) thus provides a promising micellar system that may effectively deliver anticancer agents to tumors. Furthermore, the conjugate may synergize with co-delivered drugs in the overall antitumor activity.

Disulfide linkages may, for example, further facilitate the release of FTS upon intracellular delivery to tumor cells. In that regard, cancer cells have significantly higher concentrations of glutathione (GSH) than those in the extracellular fluids, particularly the blood.

Figure 5A:
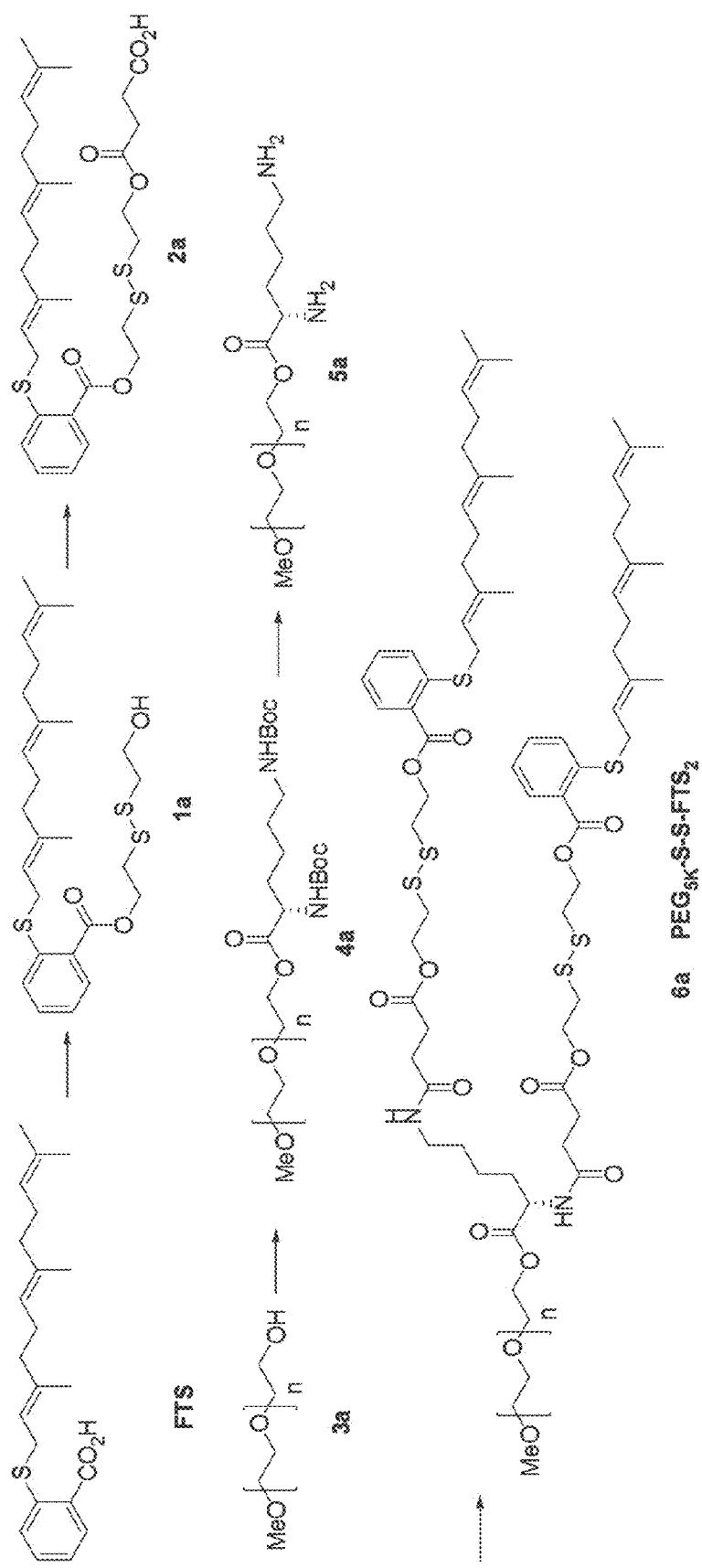
FIG. 5A illustrates an embodiment of a synthetic scheme for the synthesis of PEG$_{5K}$-SS-FTS$_2$ wherein FTS segments are attached to PEG via labile disulfide bonds.
Figures 5B, 5C:
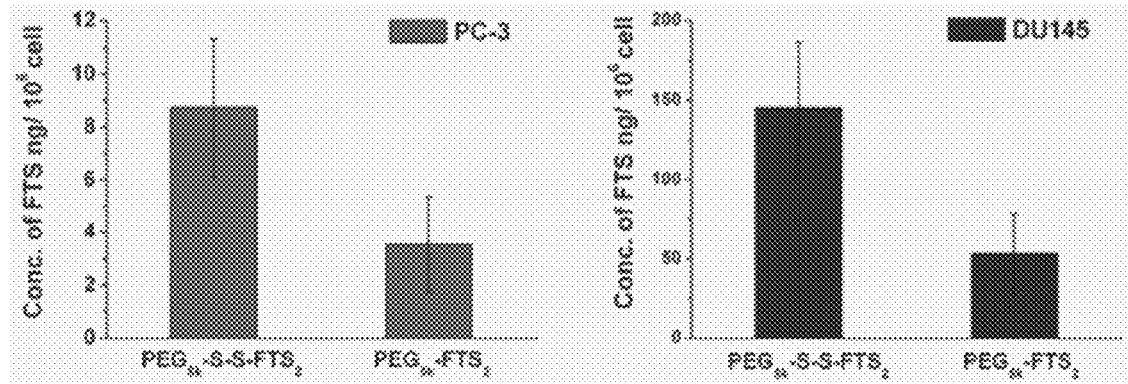
FIG. 5B illustrates HPLC-MS analysis of the amounts of released free FTS in PC-3 prostate cancer cells 72 h following treatment with PEG$_{5K}$-S—S-FTS$_2$ or PEG$_{5K}$-FTS$_2$ (at a FTS concentration of 20 μM).
FIG. 5C illustrates HPLC-MS analysis of the amounts of released free FTS in DU145 prostate cancer cells 72 h following treatment with PEG$_{5K}$-S—S-FTS$_2$ or PEG$_{5K}$-FTS$_2$ (at a FTS concentration of 20 μM).

Despite the fact that representative PEG$_{5K}$-FTS$_2$(L) carrier agents hereof demonstrate dual bioactive functionality, it would be beneficial to increase the biological activity of the system. Without limitation to any mechanism, limited bioactivity in the case of an ester linkage may, for example, be a result of limited cleavage of FTS from the carrier. Limited cleavage may occur because of: 1) the steric hindrance imposed by the PEG, and/or 2) limited esterase activity inside the cells. Facilitating cleavage of FTS from the carrier agent in, for example, tumor tissues/cells without compromising the stability of the carrier agent in the blood circulation may result in further improvement of therapeutic efficacy. A facilitated cleavage of FTS from the carrier may not only lead to release of greater amounts of biologically active free FTS, but also enhanced release of loaded drug as a result of the disassembly of the micelles following the breakdown of the PEG$_{5K}$-FTS$_2$ conjugate. Accordingly, we have developed a PEG$_{5K}$-S—S-FTS$_2$(L) conjugate into which an additional disulfide linkage was introduced. Disulfide may be used as an environment-sensitive linkage to facilitate the breakdown of a carrier agent upon reaching tumor cells or tissues. FIGS. 5B and 5C shows the results of HPLC-MS analysis of the amount of free FTS inside PC-3 or DU-145 cells 72 h following treatment with PEG$_{5K}$-FTS$_2$ (L) and PEG$_{5K}$-S—S-FTS$_2$(L) conjugate, respectively. Significantly greater amounts of released FTS were detected from cells treated with PEG$_{5K}$-S—S-FTS$_2$(L) conjugate. Free FTS was barely detectable from the cells treated with PEG$_{5K}$-FTS$_2$(S).

Figures 6A, 6B:
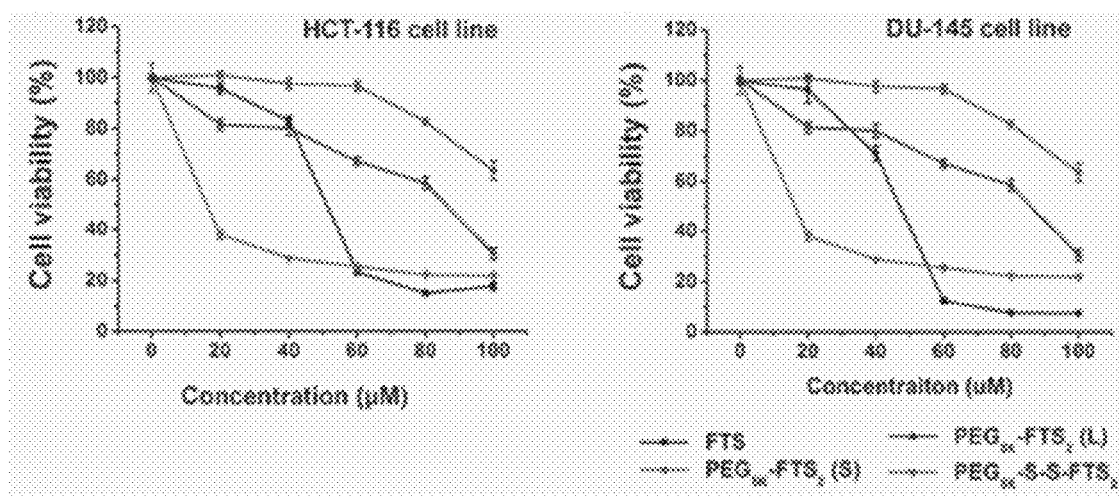
FIG. 6A illustrates cytotoxicity of PEG$_{5K}$-FTS$_2$ (L), PEG$_{5K}$-FTS$_2$ (S) and PEG$_{5K}$-S—S-FTS$_2$ in a HCT-116 human colon carcinoma cell line.
FIG. 6B illustrates cytotoxicity of PEG$_{5K}$-FTS$_2$ (L), PEG$_{5K}$-FTS$_2$ (S) and PEG$_{5K}$-S—S-FTS$_2$ in a 4T1.2 mouse breast cancer cell line.

FIGS. 6A and 6B shows the result of cytotoxicity 72 h following treatment of HCT-116 and DU-145 cancer cell lines, respectively, with the different conjugates. In agreement with previous studies, PEG$_{5K}$-FTS$_2$(L) (labile or cleavable) was more effective than PEG$_{5K}$-FTS$_2$(S) (stable) in inhibiting the growth of both HCT-116 and DU-145 cancer cells. Incorporation of an additional disulfide linkage into PEG$_{5K}$-FTS$_2$(L) led to further improvement in cytotoxicity. Interestingly, PEG$_{5K}$-S—S-FTS$_2$(L) was even more active than free FTS. Without limitation to any mechanism, this observation may, for example, be a result of enhanced intracellular delivery of FTS via PEG$_{5K}$-S—S-FTS$_2$(L).

Figure 7B:
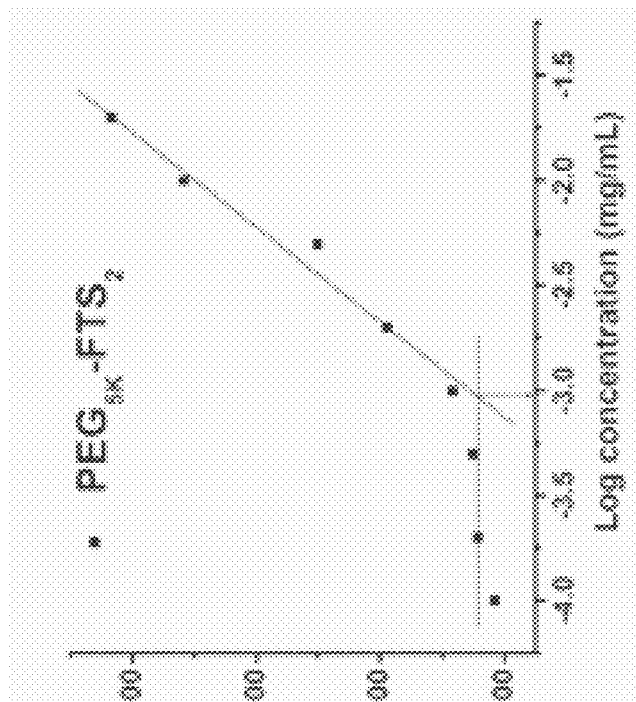
FIG. 7B illustrates a study of critical micelle concentration of PEG$_{5K}$-FTS$_2$(L) (B).
Figure 7A:
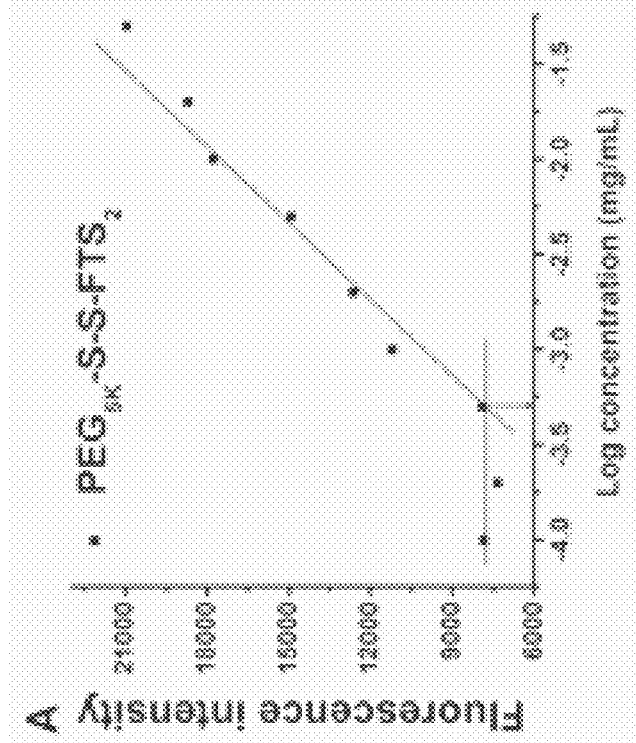
FIG. 7A illustrates a study of critical micelle concentration of PEG$_{5K}$-S—S-FTS$_2$.

FIGS. 7A and 7B shows the results of CMC measurements of PEG$_{5K}$-FTS$_2$(L) and PEG$_{5K}$-S—S-FTS$_2$(L). Surprisingly, PEG$_{5K}$-S—S-FTS$_2$(L) exhibited a CMC that was about 4 times lower than that of PEG$_{5K}$-FTS$_2$(L). Without limitation to any mechanism, this observation may, for example, be a result of a better cooperation of FTS assembly during micelle formation as a result of incorporation of a more flexible disulfide linkage. Nonetheless, a lower CMC for the PEG$_{5K}$-S—S-FTS$_2$(L) enables better colloidal stability in the blood circulation, and therefore, more effective targeting to tumors.

Figure 8B:
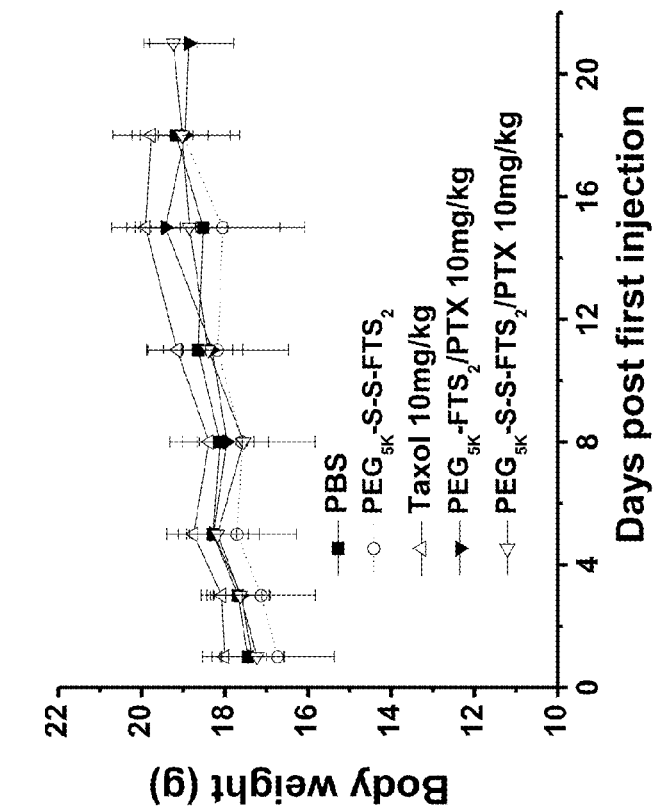
FIG. 8B illustrates changes of body weight in mice receiving different treatments
Figure 8A:
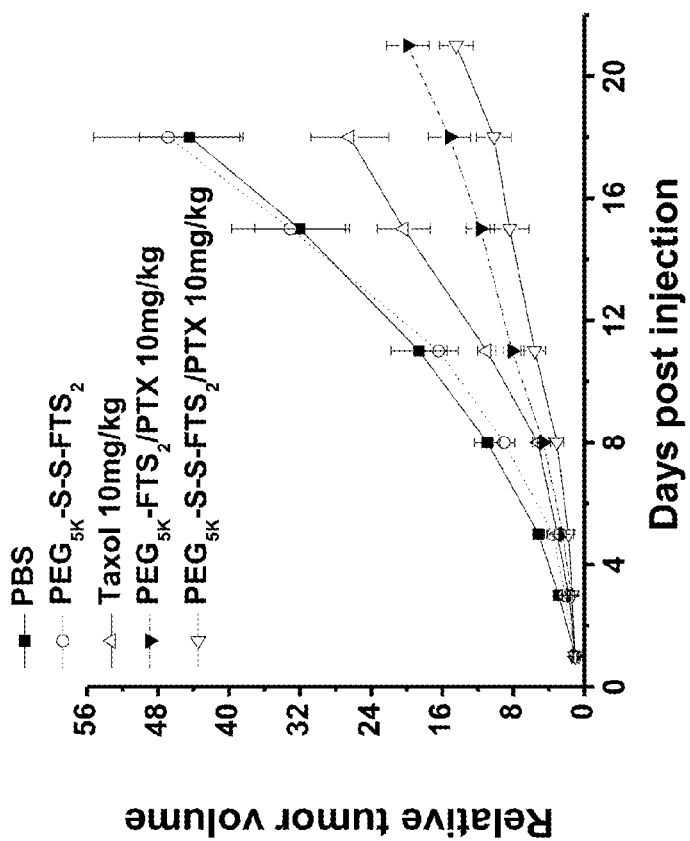
FIG. 8A illustrates antitumor activity of PTX formulated in PEG$_{5K}$-S—S-FTS$_2$ micelles in a syngeneic murine breast cancer model (4T1.2). (P<0.05 (PTX/PEG$_{5K}$-S—S-FTS$_2$ vs. PTX/PEG$_{5K}$-FTS$_2$). N=5).

FIGS. 8A and 8B shows the results of a preliminary in vivo therapy study comparing the efficacy of PTX/PEG$_{5K}$-FTS$_2$(L) with that of PTX/PEG$_{5K}$-S—S-FTS$_2$(L). It was apparent that PTX/PEG$_{5K}$-S—S-FTS$_2$(L) was more effective than PTX/PEG$_{5K}$-FTS$_2$(L) in inhibiting the growth of 4T1.2, an aggressive murine breast cancer (P<0.05).

Figure 9B:
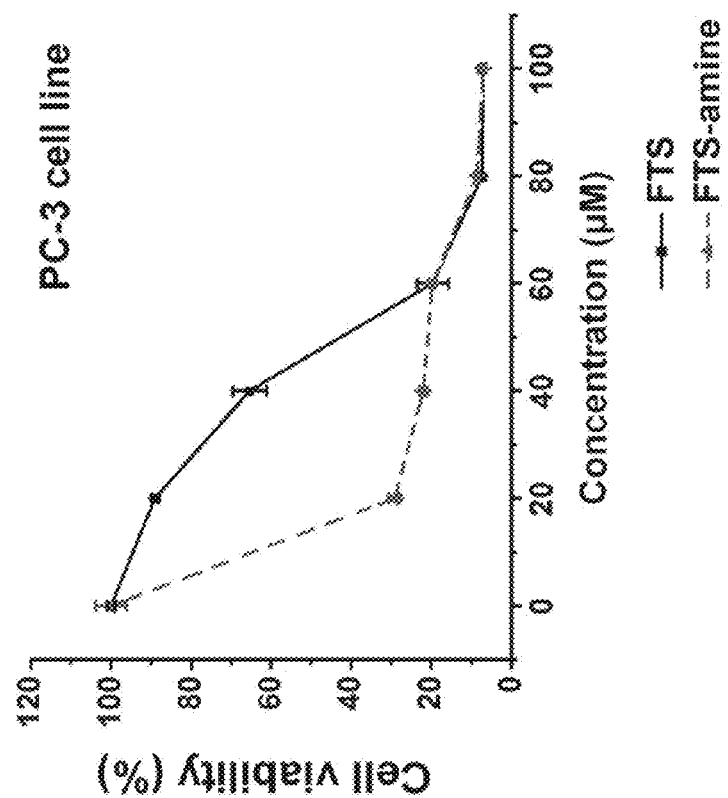
FIG. 9B illustrates cytotoxicity of FTS and FTS-amide in a PC-3 human prostate cancer cell line.
Figure 9A:
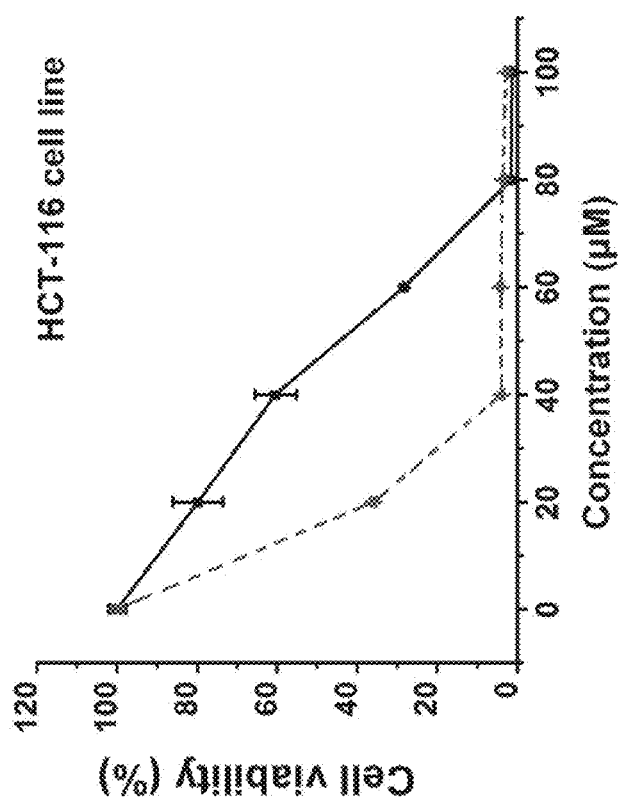
FIG. 9A illustrates cytotoxicity of FTS and FTS-amide in a HCT-116 human colon carcinoma cell line.

As described above, FTS and derivatives thereof can be used in the carrier agents hereof. In a number of embodiments (for example, for drug delivery), biologically active derivatives of FTS are used. For example, FTS-amide (illustrated below) is a FTS derivative that has been shown to be more effective than the parent compound in inhibiting the tumor cell growth both in vitro and in vivo. Similar results were obtained in our in vitro cytotoxicity study with HCT-116 and PC-3 cancer cell lines (see FIGS. 9A and 9B).

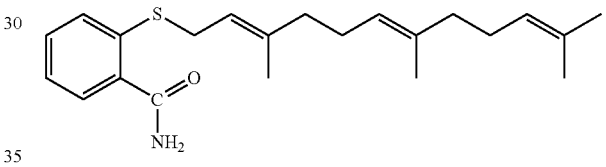

Loading of hydrophobic drugs into PEG-FTS micellar systems relies on the hydrophobic interactions between the carrier and the drug. While this mechanism works well for highly hydrophobic/lipophilic drugs, it may provide only limited effectiveness for loading of many drugs that are moderately hydrophobic. Incorporation of a compound- or drug-interactive agent, segment or motif at the interfacial region of micelles can lead to significant improvement in drug loading capacity through providing additional carrier/drug interaction mechanism. Identification and incorporation of interfacial compound/drug interactive agents in carrier agents or systems is discussed in PCT International Patent Application No. PCT/US2013/074684, the disclosure of which is incorporated herein by reference.

The compound interactive domain may, for example, include at least one amino acid group or at least one peptide group. The amino acid group or the peptide group may, for example, include at least one pendant group having an affinity for the compound. In a number of embodiments, the compound interactive domain includes at least one of a fluorenylmethyloxycarbonyl group, a carbobenzyloxy group, an isobutoxycarbamate group, a naphthylacetyl group, a carbazole group, a quinolone group, an isoquinolone group, or a group which is a residue of a molecule selected from the group of the compound, a portion of the compound or the entire compound, (9H-fluoren-9-yl)methanamine, (9H-fluoren-9-yl)methanol, 9H-fluoren-9-amine, naphthalene, 1,1'-bi-2-naphthol (BINOL), camptothecin, a camptothecin analog (for example, hydroxyl camptothecin, irinotecan, topotecan and homocamptothecins), pemetrexed, docetaxel, paclitaxel, epirubicin, doxorubicin, vinblastine, vindesine, etoposide, hydroxycamptothecin, mitoxantrone, tamoxifen, tretinoin, Vitamin A (for example, retinol, retinal, retinoic acid, and provitamin A carotenoids, such as beta-carotene), Vitamin E (for example, tocopherols and tocotrienols), Vitamin K (for example, phylloquinone or menaquinones), Vitamin D (for example, secosteroids such as cholecalciferol or ergocalciferol), curcumin, imatinib, gefitinib, erlotinib, sorafenib, and bortezomib, or a derivative thereof. In a number of embodiments, the compound interactive domain includes at least one fluorenylmethyloxycarbonyl group or a derivative thereof.

In a number of embodiments, the drug interactive group is selected from the group of a fluorenylmethyloxycarbonyl group, a carbobenzyloxy group, an isobutoxycarbamate group, a naphthylacetyl group, a carbazole group, a quinolone group, an isoquinolone group, or derivatives thereof. In a number of embodiments, the at least one group is selected from the group of a fluorenylmethyloxycarbonyl group, a carbobenzyloxy group, an isobutoxycarbamate group, a naphthylacetyl group, a carbazole group, or derivatives thereof. In a number of embodiments, the at least one group is selected from the group of a fluorenylmethyloxycarbonyl group, a carbobenzyloxy group, an isobutoxycarbamate group, a naphthylacetyl group, or a carbazole group. In a number of embodiments, the at least one group is a fluorenylmethyloxycarbonyl group or a derivative thereof. The composition may, for example, be polyethylene glycol-lysyl-(α-Fmoc-ϵ-t-Boc-lysine)$_2$.

The at least one group that interacts with the compound may, for example, have an affinity for the compound. The at least group that interacts with the compound may, for example, interact with the compound via π-π stacking, hydrophobic interaction or hydrogen-bonding.

The compound/drug-interactive segment, region or domain may, for example, be experimentally determined through, for example, solubility tests of individual motifs, such as protected amino acids or PEG-conjugates of protected amino acids that have increased water solubility. The mode of detection may, for example, be visual (for example, under a microscope) for the suppression/disappearance of crystal formation, by optical density (OD) reading, by high pressure liquid chromatography (HPLC) or any other suitable measurement method for the soluble fraction of a poorly water soluble free drug that is facilitated to form a nanostructure in aqueous solutions. Examples of groups suitable for use in interactive segments, regions or domains hereof include, but are not limited to, fluorenylmethyloxycarbonyl (FMOC), carbobenzyloxy (Cbz or Z), and isobutoxycarbamate groups as a part of a small molecule, such as amino acid derivative that is sufficiently water soluble. The compound or a portion of the compound with which the interactive segment, region or domain is to interact can also be used in the interactive segments, regions or domains. For example, reactive groups on the compound or a portion thereof (either native to the compound/portion or created thereon by modification) can be used to bond a residue of the compound/portion within the carrier agent. Motifs immobilized on solid phase support may, for example, also be useful for the identification process by, for example, binding or absorbing a particular agent to be tested compared to the unmodified solid phase support.

The motifs may, for example, additionally or alternatively be predicted theoretically based on the known structural features of a particular agent, such as charge properties, aromatic ring structures, hydrogen bonding potential, etc. A naphthylacetyl group, for example, is predicted and experimentally confirmed to be as active as an FMOC group.

Fmoc groups, derivatives thereof and similar groups (for example, carbazoles, quinolones, isoquiolones, (9H-fluoren-9-yl)methanamine, (9H-fluoren-9-yl)methanol, 9H-fluoren-9-amine, naphthalene, and Binol) in the agents hereof have, for example, been found to be active in formulating a panel of dissimilar drugs, ranging, for example, from paclitaxel, steroids, xanthene- and porphyrin-based photodynamic agents, to hydrophobic peptide drugs, with significant improvements in both drug loading capacity and drug retention. These data suggest that groups such as Fmoc qualify as a "formulation chemophors", exhibiting a potent activity in interacting with various pharmaceutical agents and thus a capability of improving carrier-drug compatibility. Without limitation to any mechanism, the molecular basis for such interaction is believed to be the result of π-π stacking interactions between the compact fused aromatic ring structure of Fmoc units and drug (or other compound) molecules bearing, for example, one or more aromatic rings, which is normally stronger than the van der Waals interaction.

The drug-interactive motifs, groups or agents may be incorporated into compositions hereof as, for example, pendant groups (for example, peptide side-chains or pending groups) on the interactive segment (at the interface region) to form designer molecules with three distinct domains: a hydrophilic head group or segment (for example, PEG), an expanded intermediate segment or interface region (interactive segment), and a hydrophobic segment, tail region or anchor region (for example, FTS). The configuration of the motif arrangement at the interface region may, for example, be continuous or discontinuous, linear or branched. The number of lipid chains may also be varied.

The carrier agents hereof may thus be tailor-designed by incorporating one or more drug-interactive motifs selected based on experimental approaches and/or theoretical predictions.

As described above, 9-Fluorenylmethoxycarbonyl or Fmoc, an amine protection group, has an unusual propensity in interacting with many type of drugs, ranging from paclitaxel, steroids, xanthene- and porphyrin-based photodynamic agents, to hydrophobic peptide drugs with linear or cyclic configuration. These agents have one or more aromatic or heterocyclic ring structures or multiple hydrophobic side chain groups (if it is a peptide derivative), and can form hydrogen bond with other molecules. These features are quite ubiquitous among many drugs and drug candidates, suggesting that this motif may have the utility for a broad spectrum of compounds. The data indicated that a compound interactive agent such as α-Fmoc behaves as a formulation chemophor or a structural unit capable of interacting with many pharmaceutical agents. The molecular basis for such propensity of interactions may, for example, arise from a combination of the fused aromatic ring structure of fluorenyl group and its carbamate and amide linkages. A fluorenyl group is a compact hydrophobic motif capable of forming hydrophobic π-π interactions with compounds carrying one or more aromatic ring structures. The carbamate and other amine linkages in the conjugate are known to facilitate hydrogen bonding interactions. Our studies hereof have shown that inclusion of a single Fmoc motif to PEG-FTS micellar system led to significant improvement (over a PEG-FTS system not including Fmoc) in the loading capacity for a number of drugs including, for example, PTX and DOX as detailed below. Carrier agents hereof may, for example, be improved via structure-activity relationship (SAR) studies. Such "improved" carrier agents hereof may then be correlated with in vivo performance with respect to pharmacokinetics and biodistribution, and the therapeutic effect in, for example, mouse tumor models.

Figure 10A:
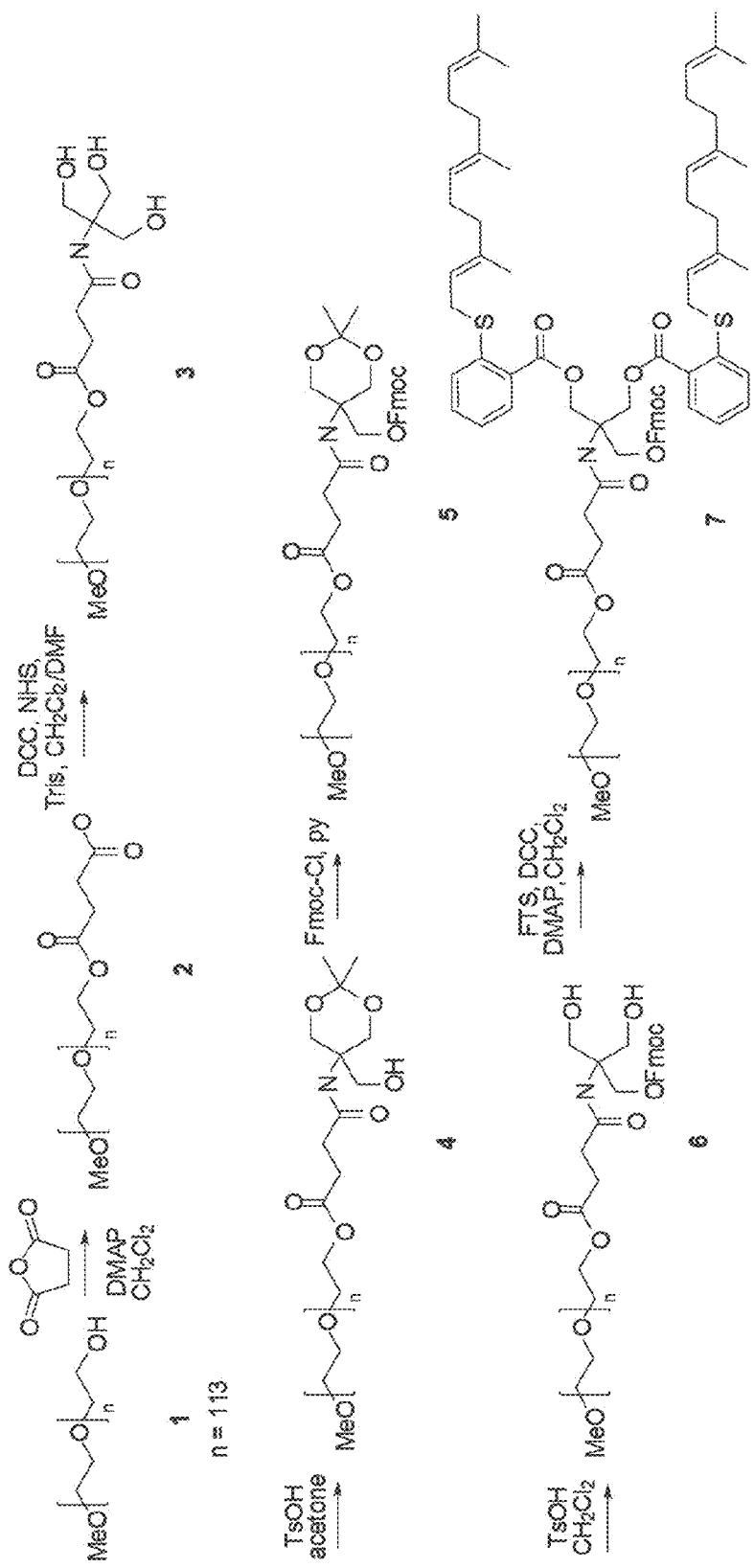
FIG. 10A illustrates an embodiment of a synthetic scheme for PEG$_{5K}$-Fmoc-FTS$_2$.
Figure 10B:
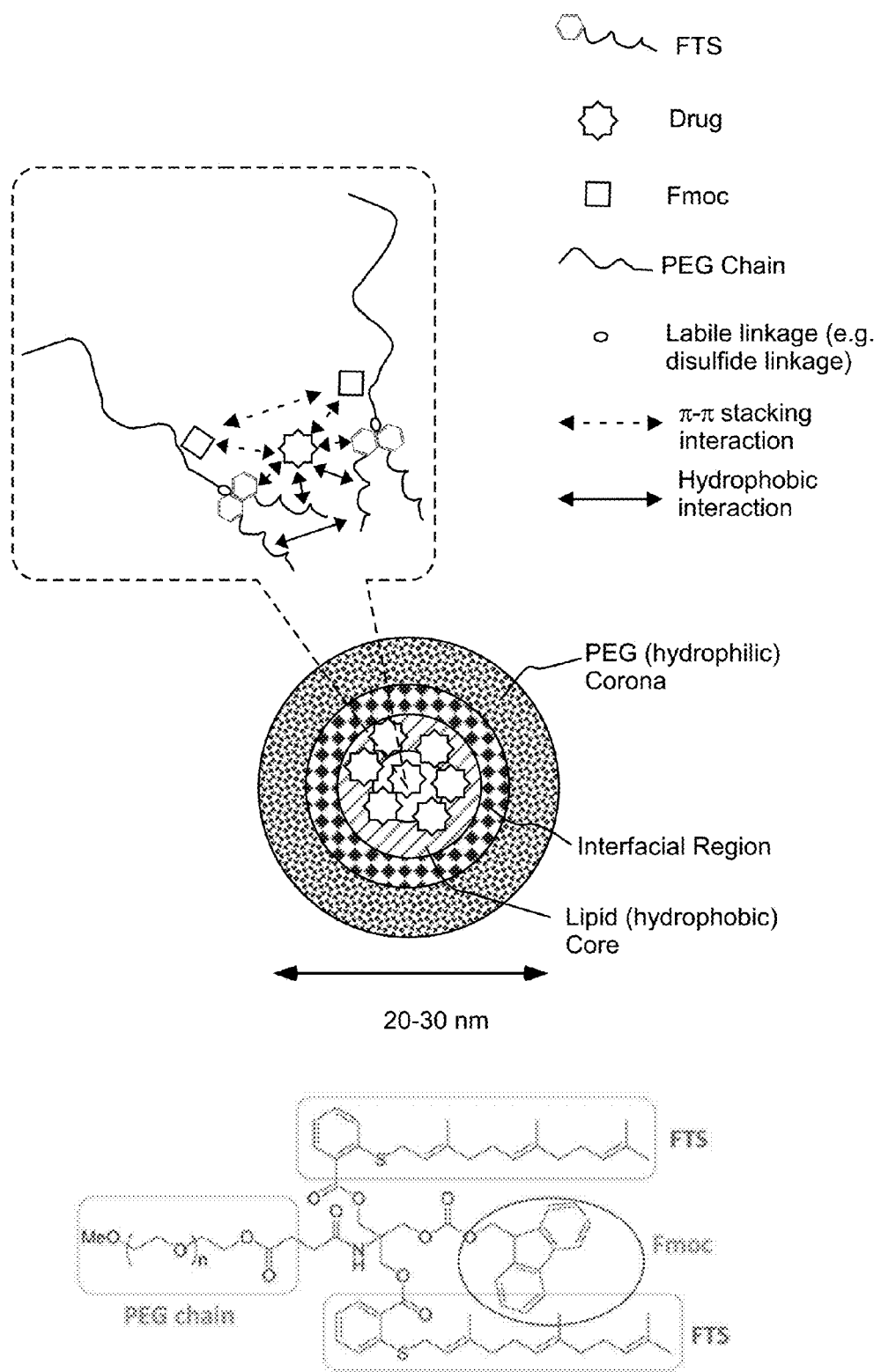
FIG. 10B illustrates an embodiment of an idealized schematic representation of a drug-loaded micelle hereof and a postulated model of carrier/drug interaction.
Figure 17A:
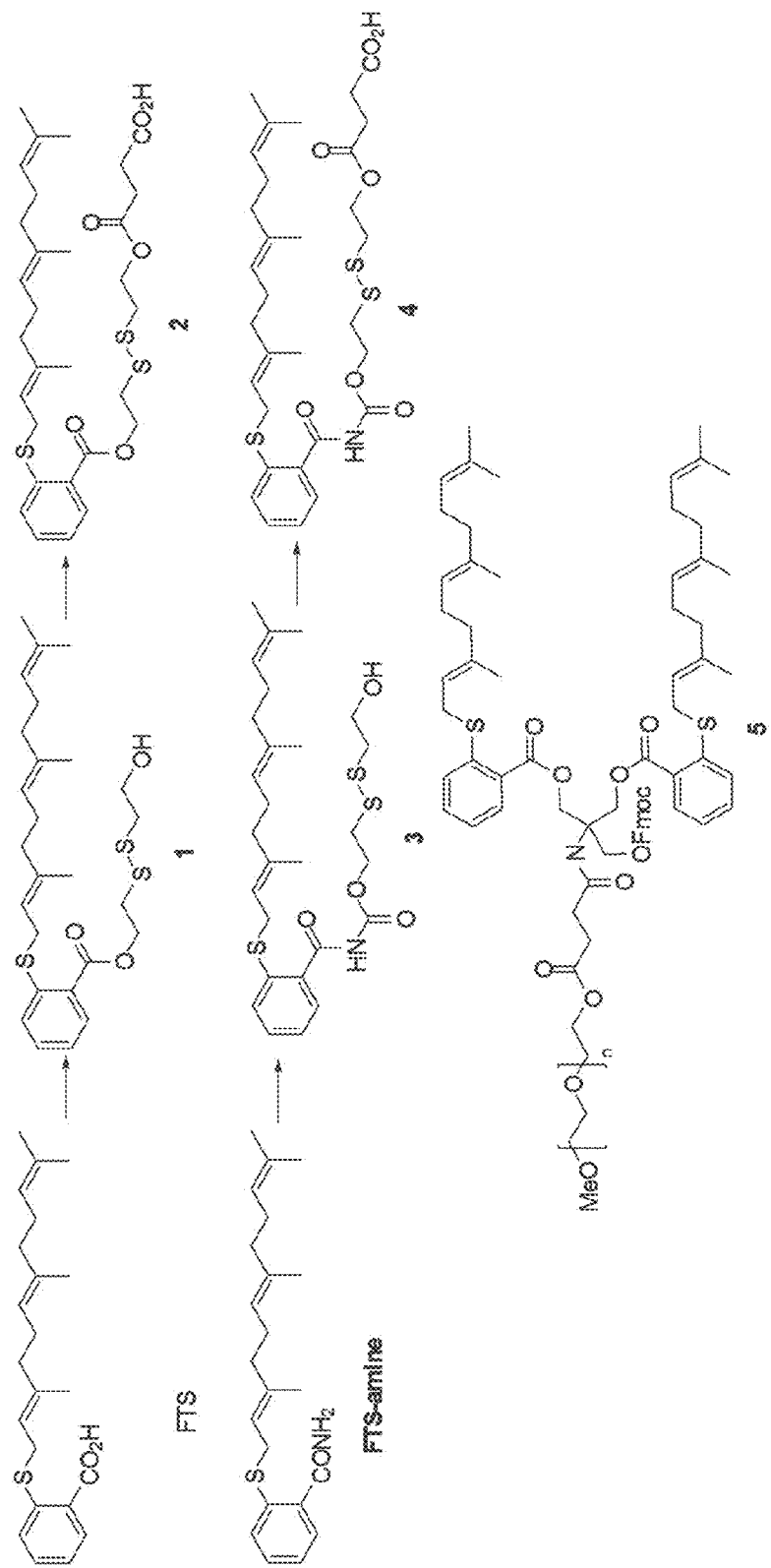
FIG. 17A(i) illustrates a number of embodiments of schemes for the synthesis of various Fmoc-containing PEG-FTS (FTS-amide) conjugates.
Figure 17B:
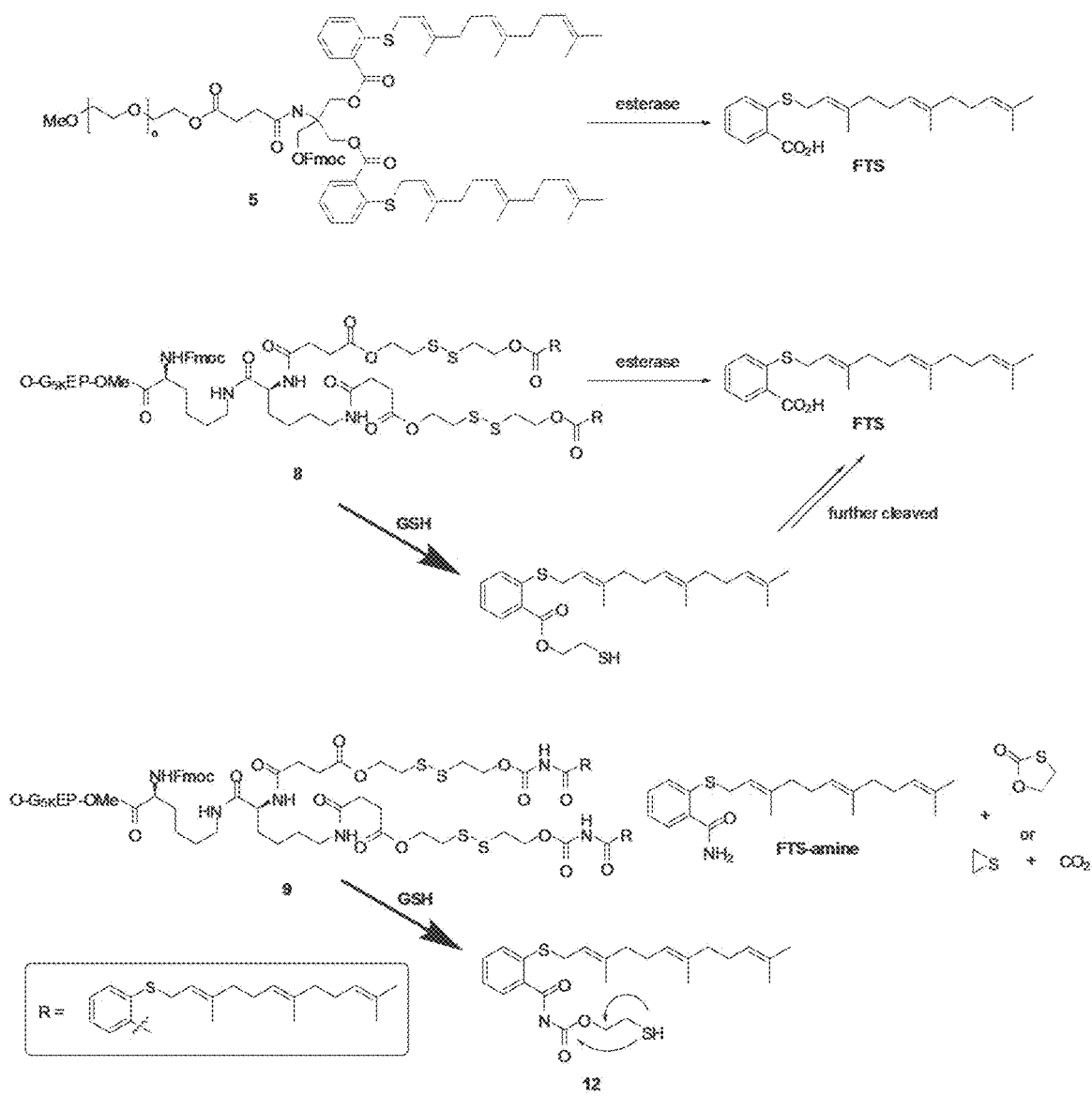
FIG. 17B illustrates a number of proposed mechanisms for the release of FTS or FTS-amide from different conjugates following intracellular delivery to, for example, tumor cells.

As described above, we have shown that inclusion of an Fmoc motif led to significant improvement in both DLC and formulation stability for a number of drugs. Increasing the number of Fmoc motif (for example, from 1 to 2) (see, FIGS. 10A and 10B) may, for example, lead to further improvement of the carrier agents hereof. The incorporation of an additional disulfide linkages on the Fmoc-containing PEG-FTS carriers may also impact carrier agent performance. Without limitation to any mechanism, FTS may, for example, be released from the $PEG_{5K}$-S—S-$FTS_2$ conjugates via two different pathways as illustrated in FIG. 17B. One pathway is direct cleavage of the ester linkage adjacent to FTS to generate the parent FTS. The other pathway involves reduction of the disulfide linkage first, followed by cleavage of the ester linkage to generate the parent FTS (see FIG. 17). The fact that significantly greater amounts of parent FTS were released from cells treated with $PEG_{5K}$-S—S-$FTS_2$(L) (see FIGS. 5B and 5C) suggest that the latter pathway is the major mechanism for FTS release. Direct release of FTS from $PEG_{5K}$-$FTS_2$(L) by intracellular esterases may be less effective as a result of the steric hindrance imposed by PEG. On the other hand, cleavage of disulfide linkage is a more effective process inside tumor cells as a result of the significantly increased GSH levels in tumor cells FIG. 10A illustrates synthesis of an Fmoc-containing PEG5k-$FTS_2$ conjugate wherein each of the FTS segments are conjugated via a labile ester bond. As illustrated in FIG. 10A, $PEG_{5K}$-Fmoc-$FTS_2$ conjugate, containing one Fmoc motif and two molecules of FTS coupled to one molecule of PEG via a labile ester linkage, was synthesized via solution condensation reactions. FIG. 10B illustrates an idealized schematic representation of a drug-loaded micelle hereof and a postulated model of carrier/drug interaction with a drug-interactive agent such as Fmoc and a hydrophobic domain including FTS.

Similar to $PEG_{5K}$-$FTS_2$ micellar system, the $PEG_{5K}$-Fmoc-$FTS_2$ conjugate readily formed micelles in aqueous solution. DLS measurements showed that $PEG_{5K}$-Fmoc-$FTS_2$ micelles had hydrodynamic sizes around 20 nm at the concentration of 20 mg/mL. TEM showed spherical particles with a relatively uniform size distribution. $PEG_{5K}$-Fmoc-$FTS_2$ micelles were highly effective in solubilizing various anticancer drugs such as PTX, doxorubicin (DOX), and many others. The size, DLC, DLE, and colloidal stability of drug-loaded $PEG_{5K}$-Fmoc-$FTS_2$ micelles were then examined and compared to those of the counterparts without an Fmoc motif. In general, incorporation of DOX or PTX led to an increase in the particle sizes for both micellar systems. However, the sizes gradually became close to the original size with the increase in carrier/drug molar ratio. For DOX, a minimal carrier/drug molar ratio of 0.5:1 was needed to formulate the drug in $PEG_{5K}$-$FTS_2$ micelles. In contrast, DOX could be loaded into $PEG_{5K}$-Fmoc-$FTS_2$ micelles at a carrier/drug molar ratio as low as 0.1:1. The DLC for DOX/$PEG_{5K}$-Fmoc-$FTS_2$ mixed micelles at this carrier/drug ratio is 32.8%, which represents a 3.2-fold increase compared with the $PEG_{5K}$-$FTS_2$ formulation. In addition, DOX/$PEG_{5K}$-Fmoc-$FTS_2$ mixed micelles were significantly more stable than the counterparts without an Fmoc motif under all carrier/drug ratios examined. Similarly, incorporation of an Fmoc motif significantly improved the performance of $PEG_{5K}$-Fmoc-$FTS_2$ micelles in formulating PTX. The DLC for PTX/$PEG_{5K}$-Fmoc-$FTS_2$ mixed micelles was 12.1%, which is a 2.7-fold increase compared with the counterpart without an Fmoc. The morphology and size uniformity were largely retained following loading of PTX or DOX at a respective molar ratio of 2.5:1 and 1:1. Without limitation to any mechanism, the improvements in drug-loading capacity and formulation stability are likely a result of an enhanced drug/carrier interaction. As described above, the Fmoc group contains a bulky, fused fluorenylmethyl ring structure capable of providing strong hydrophobic interaction and forming π-π stacking with compounds carrying aromatic moieties. Thus, in addition to hydrophobic interaction, $PEG_{5K}$-Fmoc-$FTS_2$ can further interact with PTX or DOX through π-π stacking, leading to improved carrier/drug compatibility.

The CMC of $PEG_{5K}$-Fmoc-$FTS_2$ micelles was examined using pyrene as a fluorescence probe. The CMC of the $PEG_{5K}$-Fmoc-$FTS_2$ micelles was 0.2 µM, which is lower than that of $PEG_{5K}$-$FTS_2$ micelles (0.68 µM). This result may, for example, be a result of the fact that Fmoc can not only enhance the carrier/drug interaction, but also facilitate the interaction among the carrier molecules themselves. In any event, the reduced CMC may improve the stability of $PEG_{5K}$-Fmoc-$FTS_2$ micelles upon dilution in vivo.

Figure 11:
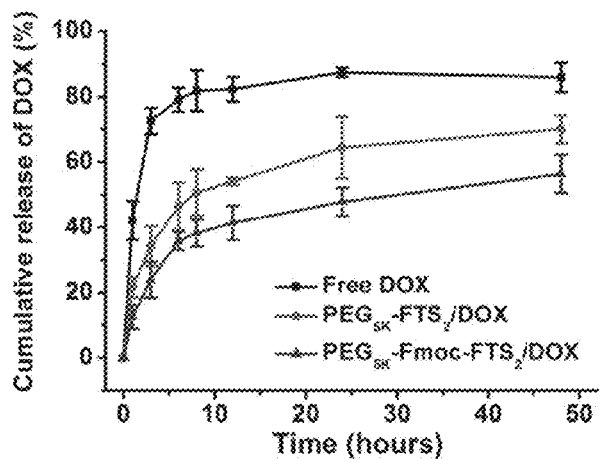
FIG. 11 illustrates cumulative doxorubicin (DOX) release profile from free DOX, DOX-loaded PEG$_{5K}$-FTS$_2$, and PEG$_{5K}$-Fmoc-FTS$_2$ micelles. DPBS ((pH=7.4) containing 0.5% (w/v) Tween 80 was used as the release medium, wherein values reported are the means±SD for triplicate samples).

The profile of DOX release from $PEG_{5K}$-Fmoc-$FTS_2$ micelles was studied by a dialysis method and compared to that of DOX-loaded $PEG_{5K}$-$FTS_2$ micelles. For the initial 8 h, about 50.7% of DOX was released from $PEG_{5K}$-$FTS_2$ formulation while only 38.3% of DOX was released from DOX-loaded $PEG_{5K}$-Fmoc-$FTS_2$ micelles (see FIG. 11). Overall, DOX formulated in $PEG_{5K}$-Fmoc-$FTS_2$ micelles exhibited a slower relative rate of DOX release compared to the counterpart without an Fmoc motif. Hemolytic activities of drug-free $PEG_{5K}$-Fmoc-$FTS_2$ micelles and polyethylenimine (PEI), a cationic polymer known to have significant hemolytic effect were also studied. PEI induced hemolysis in a dose-dependent manner. In contrast, $PEG_{5K}$-Fmoc-$FTS_2$ micelles showed only negligible levels of hemolytic activity at the same experimental concentrations, suggesting a safe profile of $PEG_{5K}$-Fmoc-$FTS_2$ micelles.

Figure 12A:
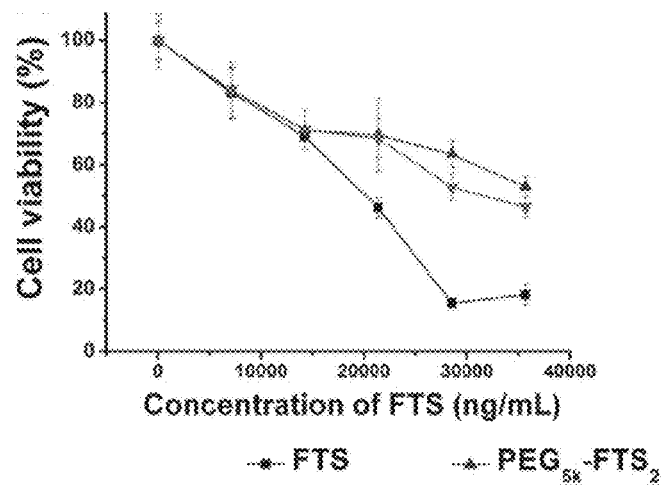
FIG. 12A illustrates cytotoxicity studies of drug-free PEG$_{5K}$-FTS$_2$ and PEG$_{5K}$-Fmoc-FTS$_2$ micelles compared to FTS against a 4T1.2 mouse breast cancer cell line.
Figure 12B:
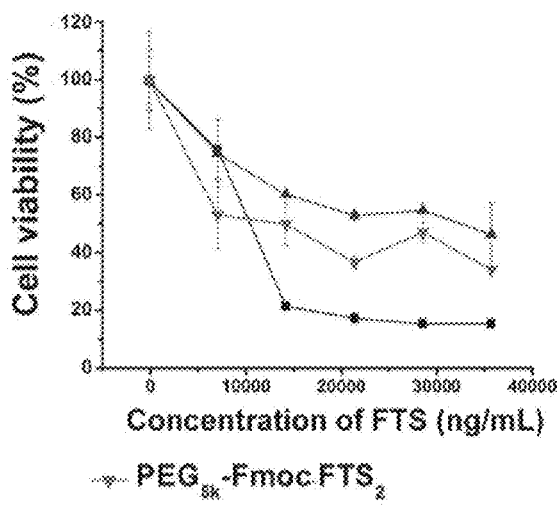
FIG. 12B illustrates cytotoxicity studies of drug-free PEG$_{5K}$-FTS$_2$ and PEG$_{5K}$-Fmoc-FTS$_2$ micelles compared to FTS against a HCT-116 human colon carcinoma cell line.

The cytotoxicity of drug-free $PEG_{5K}$-Fmoc-$FTS_2$ and $PEG_{5K}$-$FTS_2$ micelles was examined in 4T1.2 and HCT-116 tumor cells and compared to free FTS (see FIGS. 12A and 12B, respectively). Free FTS inhibited the tumor cell growth in a concentration-dependent manner. The two FTS conjugates were comparable but slightly less active than free FTS in cytotoxicity towards both 4T1.2 and HCT-116 tumor cells (see FIGS. 12A and 12B, respectively). The cytotoxicity of $PEG_{5K}$-Fmoc-$FTS_2$ is unlikely to be attributed to the surface activity since PEG-Fmoc-$FTS_2$ micelles showed minimal hemolytic activity at the concentrations that were much higher than those used in the cytotoxicity study. Without limitation to any mechanism, it is likely that the cytotoxicity of PEG-FTS comes from the released FTS following intracellular delivery. This mechanism is supported by the observation that a $PEG_{5K}$-$FTS_2$ conjugate with a relatively labile ester linkage is more active than a similar conjugate with a relatively stable amide linkage.

FIGS. 13A-C show the cytotoxicity of TAXOL and PTX formulated in $PEG_{5K}$-Fmoc-$FTS_2$ micelles in several cancer cell lines. TAXOL inhibited the tumor cell growth in a concentration dependent manner. Delivery of PTX via $PEG_{5K}$-Fmoc-$FTS_2$ micelles led to a significant increase in the cytotoxicity at low concentrations. We also tested the cytotoxicity of DOX formulated in $PEG_{5K}$-Fmoc-$FTS_2$ micelles and compared to free DOX.HCl. Similarly, DOX-loaded $PEG_{5K}$-Fmoc-$FTS_2$ micelles showed more potent cytotoxicity than free DOX at the low concentration range studied (see FIGS. 13D-F). When PTX or DOX was formulated into the PEG$_{5K}$-Fmoc-FTS$_2$ micelles, they showed higher levels of cytotoxicity to MCF-7 human breast carcinoma cell line, A549 human lung adenocarcinoma epithelial cell line, and HCT-116 cancer cell line compared with TAXOL formulation or free DOX (see FIGS. 13A-F), indicating that PTX or DOX can be more effectively delivered into tumor cells by PEG$_{5K}$-Fmoc-FTS$_2$ micelles, resulting in enhanced tumor cell killing.

Groups of 4 female CD-1 mice were administered intravenously with a single dose of either TAXOL (15-25 mg PTX/kg) or PTX-loaded PEG$_{5K}$-Fmoc-FTS$_2$ micelles (50-140 mg PTX/kg). TAXOL was well tolerated at the dose of 15 mg PTX/kg. However, increasing the PTX dosage to 20 mg/kg resulted in the death of 1 out of 4 treated mice. For the mice treated with PTX-loaded PEG$_{5K}$-Fmoc-FTS$_2$ micelles, there was neither significant weight loss nor noticeable changes in normal activity at a PTX dosage as high as 140 mg/kg. Therefore, the MTD for PTX/PEG$_{5K}$-Fmoc-FTS$_2$ is greater than 140 mg/kg, which is significantly higher than that for TAXOL (15-20 mg/kg). Maximum Tolerated Dose studies DOX-loaded PEG$_{5K}$-Fmoc-FTS$_2$ micelles indicated that there were no obvious body weight loss and other toxicity signs in the mice treated with DOX-loaded PEG$_{5K}$-Fmoc-FTS$_2$ micelles at the doses of 5-15 mg DOX/kg within two weeks. Only a moderate body weight loss (<10%) was found in mice treated with 20 mg/kg of DOX/PEG$_{5K}$-Fmoc-FTS$_2$ mixed micelles on day 4, which was recovered on day 5. In contrast, although free DOX was well tolerated at the dose of 10 mg/kg, it caused a significant decrease (>15%) in the body weight, and eventually the death of all treated mice at a dose of 15 mg DOX/kg (Table S3). Thus, the MTDs of DOX-loaded PEG$_{5K}$-Fmoc-FTS$_2$ micelles and free DOX are ~20 mg/kg and 10 mg/kg, respectively. Without limitation to any mechanism, the improved safety profile of PEG$_{5K}$-Fmoc-FTS$_2$ formulation may be a result of a slower rate of drug release from the micelles before they reach the tumor site, leading to reduced drug uptake by normal tissues.

Biodistribution and tumor-targeting efficiency of PEG$_{5K}$-Fmoc-FTS$_2$ micelles were tested in a human prostate cancer xenograft model (PC-3). DiD, a hydrophobic near infrared fluorescence (NIRF) dye with high penetration, low tissue absorption and scattering was loaded into the PEG$_{5K}$-Fmoc-FTS$_2$ micelles for tissue imaging. The results showed that DiD-loaded PEG$_{5K}$-Fmoc-FTS$_2$ micelles were able to accumulate at the tumor as early as 6 h post injection, and these micelles retained in the tumor at 96 h after injection. No obvious tumor accumulation was observed in the mice treated with free DiD dye. After last imaging at 96 h post-injection, tumors and major organs were excised for ex vivo imaging. Significantly higher levels of signal were observed in the tumor tissues compared with normal organs except the lung. Without limitation to any mechanism, the small size of the micellar systems hereof contribute significantly to the effective tumor localization. Once again, it has been reported that the size of the particles needs to be within sub-100 nm range for them to efficiently reach the poorly vascularized tumors. Such small sizes are also critical to enable the particles effective in deep penetration into the tumor tissues, especially the tumors with a tough tangle of collagen such as pancreatic and some breast cancers. Little fluorescence signal was observed in liver and spleen, the two major internal organs that are involved in the nonspecific clearance of nanoparticles. Without limitation to any mechanism, the low signal in the liver may be a result of a combination of a) very low uptake of the particles resulting from their small sizes; and b) rapid metabolism of the particles in the liver.

Figure 14A:
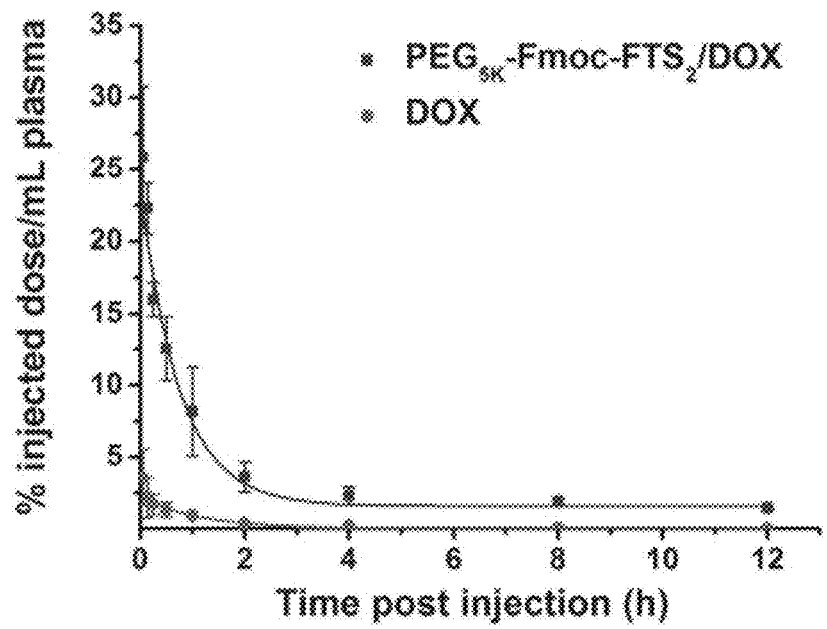
FIG. 14A illustrates a study of blood retention kinetics of DOX.HCl and DOX-loaded PEG$_{5K}$-Fmoc-FTS$_2$ micelles in mice, wherein DOX.HCl and DOX-loaded PEG$_{5K}$-Fmoc-FTS$_2$ micelles were injected into female BALB/c mice via tail vein at a dose of 5 mg DOX/kg.

In studied of plasma pharmacokinetics, free DOX.HCl and DOX-loaded PEG$_{5K}$-Fmoc-FTS$_2$ micelles were injected to tumor-free mice at a dose of 5 mg/kg, and the DOX concentration in plasma was measured at different time points. At this dose, the initial plasma concentration of the carrier is ~0.6 µM, which is significantly higher than its CMC (0.2 µM). FIG. 14A shows the % of injected dose of DOX in the blood over time following i.v. administration. The pharmacokinetic parameters were calculated based on a non-compartment model and summarized in Table 2. The $T_{1/2}$ of DOX in DOX-loaded PEG$_{5K}$-Fmoc-FTS$_2$ micelles was 6.67-fold higher than that of free DOX. Furthermore, the plasma AUC$_{0-inf}$ of DOX for the micellar DOX was almost 19-fold higher than that of free DOX (64.8 vs 3.43 µg×h/mL). In contrast, the Vd of DOX for micellar DOX was significantly lower than that of free DOX (2.58 vs 7.34 L/kg), suggesting prolonged blood circulation of DOX-loaded PEG$_{5K}$-Fmoc-FTS$_2$ micelles.

TABLE 2

| Groups | $T_{1/2}$ (h) | AUC$_{0-inf}$ (µg × h/mL) | Cmax (µg/mL) | CL (L/h/kg) | Vd (L/kg) |
|---|---|---|---|---|---|
| DOX | 1.74 | 3.43 | 3.59 | 2.91 | 7.34 |
| PEG$_{5K}$-Fmoc-FTS$_2$/DOX | 11.60 | 64.80 | 25.84 | 0.15 | 2.58 |

Figure 14B:
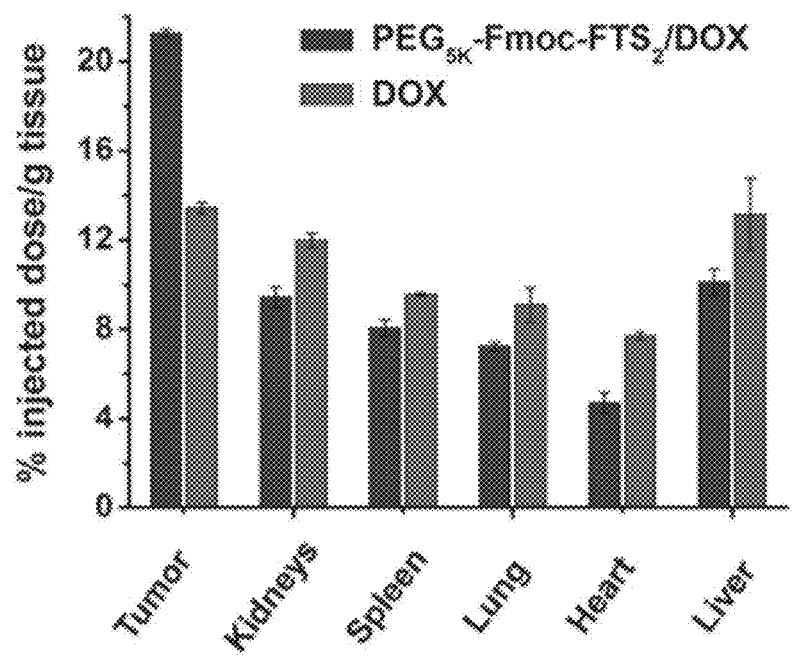
FIG. 14B illustrates a study of tissue distribution of DOX 1 day following injection, wherein DOX.HCl and DOX-loaded PEG$_{5K}$-Fmoc-FTS$_2$ were injected into female BALB/c mice bearing 4T1.2 breast tumor at the dose of 5 mg DOX/kg, respectively and values are means±SEM.

The tissue distribution of DOX.HCl and DOX-loaded PEG$_{5K}$-Fmoc-FTS$_2$ micelles was also investigated in female BALB/c mice bearing 4T1.2 breast tumor. Free DOX.HCl and DOX-loaded PEG$_{5K}$-Fmoc-FTS$_2$ micelles were injected at the same DOX dose of 5 mg/kg. At 24 h post-injection, major organs and tumors were excised for DOX determination. As shown in FIG. 14B, there was about 2-fold increase in the tumor uptake of DOX for DOX-loaded PEG$_{5K}$-Fmoc-FTS$_2$ micelles compared to free DOX. Without limitation to any mechanism, the enhanced DOX accumulation may be a result of the small size of the DOX-loaded micelles and their excellent stability. In addition, DOX-loaded PEG$_{5K}$-Fmoc-FTS$_2$ micelles were associated with a reduced DOX accumulation in normal organs such as heart compared to free DOX (see FIG. 7B). These findings showed that DOX-loaded PEG$_{5K}$-Fmoc-FTS$_2$ increases the tumor-target efficacy of DOX, but also decreases DOX-associated cardiotoxicity.

Figure 15A:
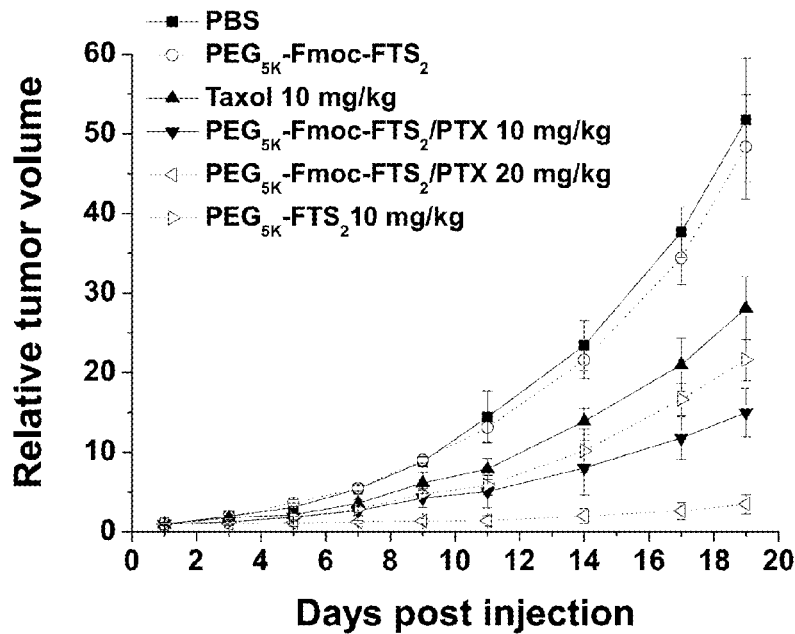
FIG. 15A illustrates a study of enhanced antitumor activity of PTX formulated in PEG$_{5K}$-Fmoc-FTS$_2$ micelles in a syngeneic murine breast cancer model (4T1.2).

The in vivo antitumor activity of PTX- and DOX-loaded PEG$_{5K}$-Fmoc-FTS$_2$ micelles was first investigated in a syngeneic murine breast cancer model (4T1.2). As shown in FIG. 15A, free PEG$_{5K}$-Fmoc-FTS$_2$ micelles alone showed little effect in inhibiting the tumor growth at the dose used. Taxol formulation showed a modest effect in inhibiting the tumor growth at a dose of 10 mg PTX/kg. In contrast, PTX formulated in PEG$_{5K}$-Fmoc-FTS$_2$ micelles showed a much more pronounced antitumor activity at the same dosage. It is also apparent that PTX/PEG$_{5K}$-Fmoc-FTS$_2$ mixed micelles were more active than the counterpart without an Fmoc motif (P<0.05). Increasing the PTX dosage to 20 mg/kg resulted in a further improvement in the therapeutic effect.

Figure 15B:
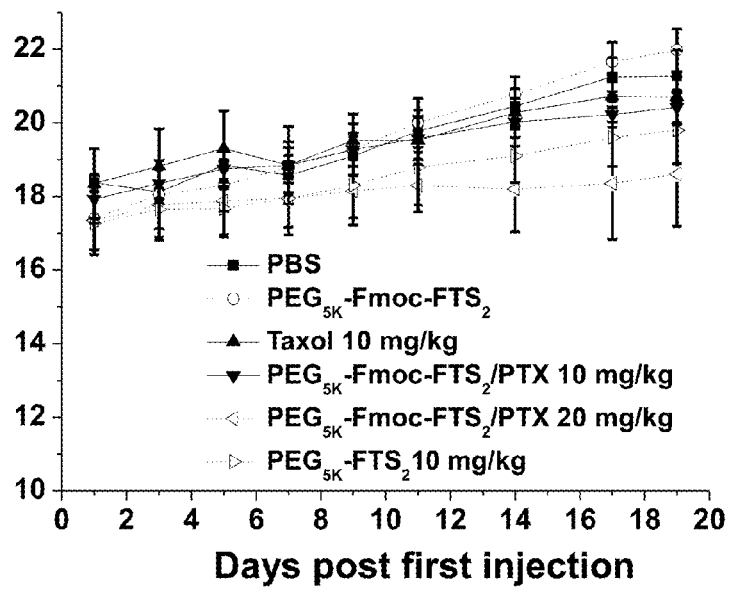
FIG. 15B illustrates a study of changes of body weight in mice that received different treatments, wherein P<0.01 (10 mg PTX/kg PEG$_{5K}$-Fmoc-FTS$_2$ vs Taxol), P<0.05 (10 mg PTX/kg PEG$_{5K}$-Fmoc-FTS$_2$ vs 10 mg PTX/kg PEG$_{5K}$-FTS$_2$).
Figure 15C:
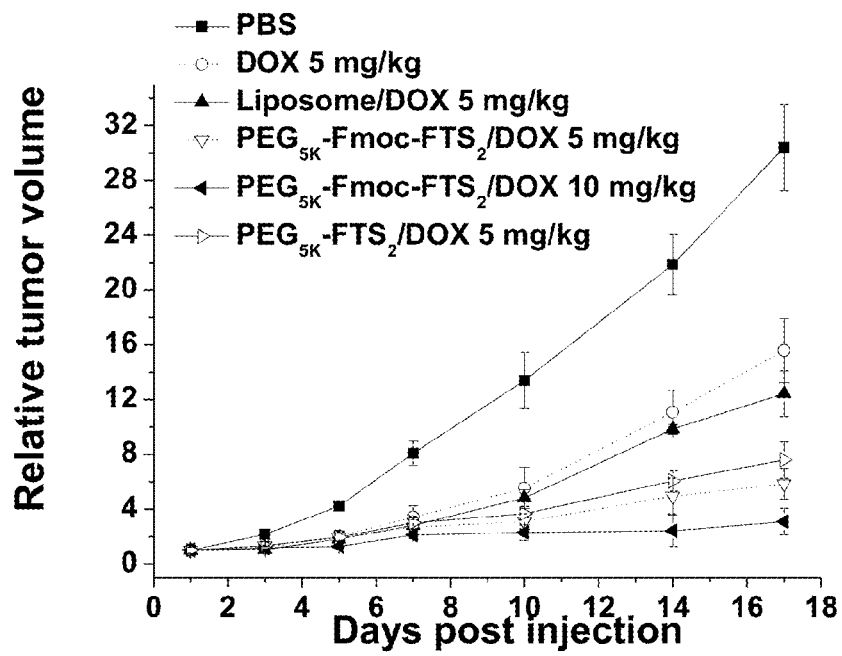
FIG. 15C illustrates a study of enhanced antitumor activity of DOX formulated in PEG$_{5K}$-Fmoc-FTS$_2$ micelles in a syngeneic murine breast cancer model (4T1.2) compared to DOX.HCl and DOX-loaded liposome.

FIG. 15C shows the result of therapy study on DOX/PEG$_{5K}$-Fmoc-FTS$_2$ mixed micelles in 4T1.2 tumor model. Both DOX/PEG$_{5K}$-FTS$_2$ and DOX/PEG$_{5K}$-Fmoc-FTS$_2$ were significantly more active than free DOX or liposomal DOX in inhibiting the tumor growth. There was also a trend of improvement in antitumor activity for DOX/PEG$_{5K}$-

Figure 15D:
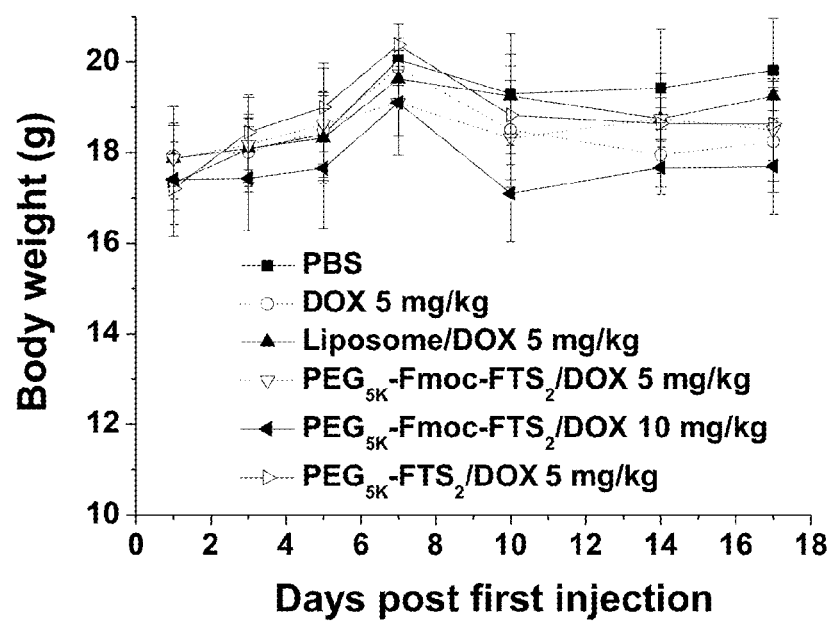
FIG. 15D illustrates a study of changes of body weight in mice that received different treatments, wherein P<0.01 (5 mg DOX/kg PEG$_{5K}$-Fmoc-FTS$_2$ vs DOX.HCl), P<0.01 (5 mg DOX/kg PEG$_{5K}$-Fmoc-FTS$_2$ vs 5 mg DOX/kg liposome).

Fmoc-FTS$_2$ compared to DOX/PEG$_{5K}$-FTS$_2$ although it is not statistically significant (P=0.16). No significant changes were noticed in body weight in all treatment groups compared to PBS control group (see FIGS. 15B and 15D).

Figure 16A:
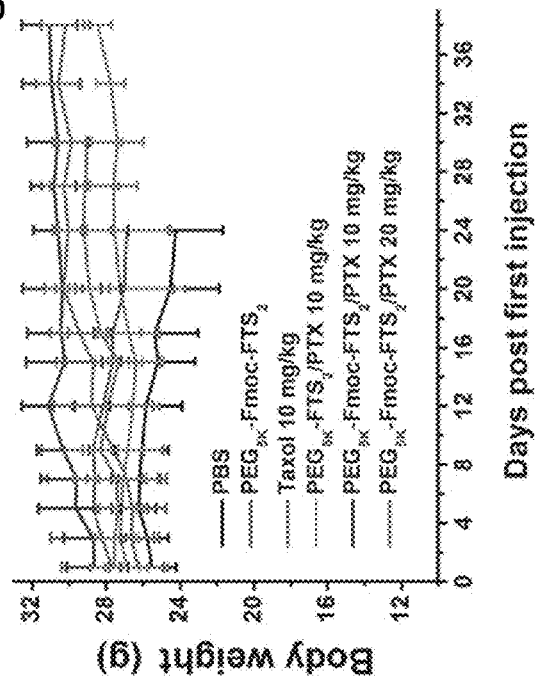
FIG. 16A illustrates a study of enhanced antitumor activity of PTX formulated in PEG$_{5K}$-Fmoc-FTS$_2$ micelles in a human prostate cancer xenograft model (PC-3).
Figure 16B:
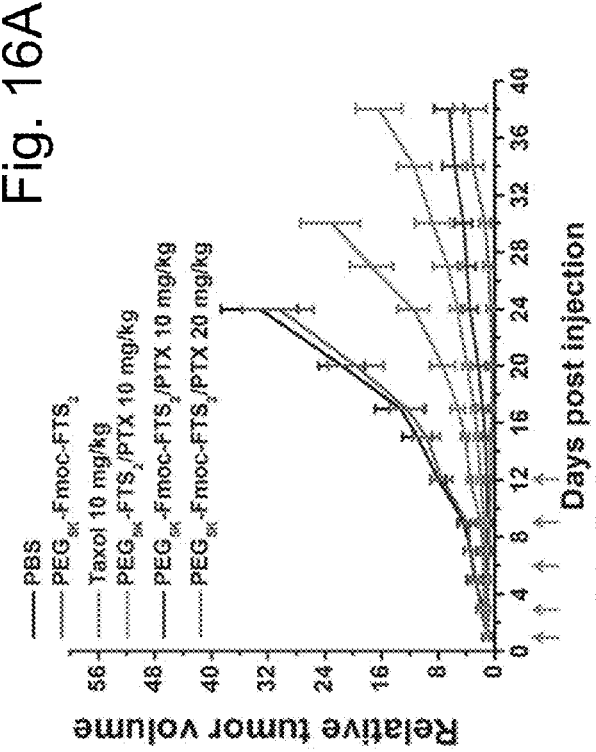
FIG. 16B illustrates a study of changes of body weight in mice that received different treatments, wherein P<0.01 (10 mg PTX/kg PEG$_{5K}$-Fmoc-FTS$_2$ vs Taxol), P<0.01 (10 mg PTX/kg PEG$_{5K}$-Fmoc-FTS$_2$ vs 10 mg PTX/kg PEG$_{5K}$-FTS$_2$).
Figure 16C:
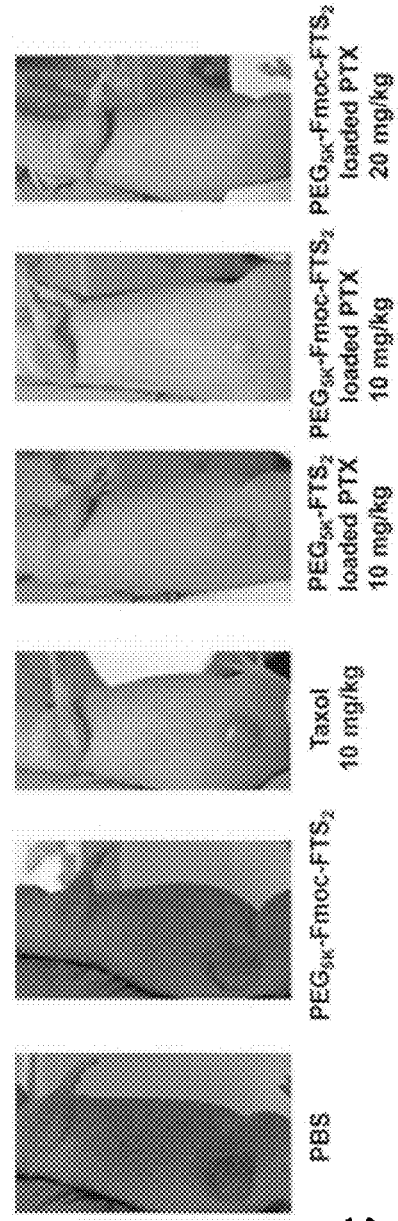
FIG. 16C illustrates photographs of representative images of nude mice bearing PC-3 tumors treated with PBS and different PTX formulations by day 17 after initial treatment.

As illustrated in FIG. 16A, the in vivo therapeutic activity of PTX formulated in PEG$_{5K}$-Fmoc-FTS$_2$ micelles was further evaluated in a human prostate cancer xenograft model. The PC-3 model has a relatively slower growth rate than 4T1.2 tumor model and tumor growth was more effectively controlled by the different treatments in PC-3 model. Nonetheless, PTX/PEG$_{5K}$-Fmoc-FTS$_2$ mixed micelles were significantly more effective than either Taxol or PTX/PEG$_{5K}$-FTS$_2$ mixed micelles in inhibiting the tumor growth at the same dose of 10 mg PTX/kg. FIG. 16C shows representative images of nude mice bearing PC-3 tumors treated with PBS and various PTX formulations by day 17 after initial treatment. By day 17, the RTV for PTX/PEG$_{5K}$-Fmoc-FTS$_2$ mixed micelles was 1.71, while the RTVs for mice treated with Taxol and PTX/PEG$_{5K}$-FTS$_2$ mixed micelles were 5.2, and 2.9, respectively. Increasing the dose of PTX to 20 mg PTX/kg led to a further improvement in antitumor activity; one out of the 5 mice in this group became tumor-free after day 38 without further treatment. No weight loss was observed in mice treated with all PTX formulations (see FIG. 16B), while consistent weight loss was shown in mice treated with PBS or carrier alone after day 9 (see FIG. 16B).

In vivo therapy studies thus demonstrated that significant therapeutic effect can be achieved with minimal toxicity using our PEG$_{5K}$-Fmoc-FTS$_2$ micellar system in both prostate and breast cancer models. Without limitation to any mechanism, the superior antitumor efficacy along with the minimal toxicity of the improved system may, for example, be ascribed to the very small size of the micelles and their improved pharmacokinetic profile, leading to effective tumor targeting and reduced nonspecific uptake by normal tissues.

As set forth above, in nanomicellar systems hereof including an FTS-based hydrophobic domain, a PEG hydrophilic segment and a drug-interactive Fmoc motif, both drug loading capacity and formulation stability were significantly improved by inclusion of a drug-interactive Fmoc motif. In contrast to many existing micellar systems that have no favorable biological activity, PEG$_{5K}$-Fmoc-FTS$_2$ conjugates hereof retained the biological activity of FTS. In addition to its antitumor activity, PEG$_{5K}$-Fmoc-FTS$_2$ synergized with codelivered anticancer agents in inhibiting the cell growth. Pharmacokinetics and biodistribution studies showed that DOX-loaded PEG$_{5k}$-Fmoc-FTS$_2$ micelles were able to retain DOX in the bloodstream for a prolonged period of time and highly effective in targeted delivery of DOX to tumors. Moreover, PTX- or DOX-loaded PEG$_{5k}$-Fmoc-FTS$_2$ micelles led to a superior antitumor activity over other treatments including drugs formulated in PEG5k-FTS$_2$ micelles in both breast cancer and prostate cancer models.

Figure 17C:
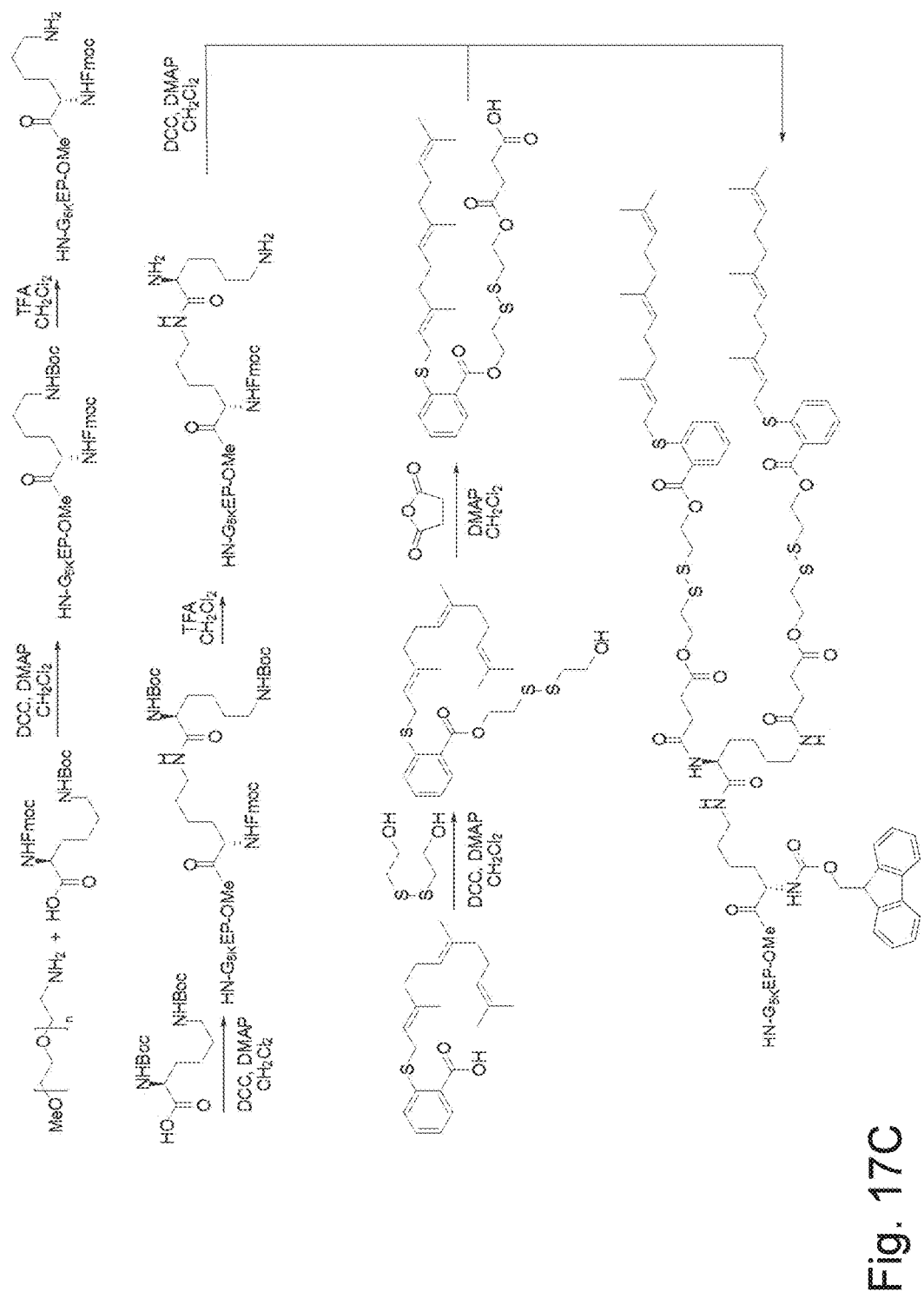
FIG. 17C illustrates another embodiment of a synthetic scheme for the synthesis of Fmoc-containing PEG-FTS conjugates.

As described above, representative studies with PEG$_{5K}$-S—S-FTS$_2$ conjugates indicate that the efficacy of composition hereof can be further enhanced via inclusion of a labile disulfide bond. FIGS. 17A(i) and 17A(ii) illustrate synthesis of two Fmoc-containing PEG$_{5K}$-S—S-FTS$_2$ conjugates (compounds 8 and 10) wherein each of the FTS segments are conjugated via labile ester and disulfide bonds, and two Fmoc-containing PEG$_{5K}$-S—S-FTS-amide$_2$ conjugates (compounds 9 and 11). FIG. 17C illustrates an alternative route to the synthesis of PEG$_{5K}$-S—S-FTS$_2$ conjugates.

As described above, FTS-amide is a more potent Ras antagonist than FTS. After the first step of reduction, the released FTS-amide derivative (compound 12 in FIG. 17B) will be rapidly converted to the parent FTS-amide via intramolecular cyclization. The release of FTS-amide from the PEG$_{5K}$-S—S-FTS-amide$_2$ conjugates may, for example, be highly efficient as it is not dependent on the intracellular esterase activity. Such a carrier agent or system may, for example, be particularly suitable for drug delivery to tumors with low esterase activity.

Polymer-assisted liquid phase synthesis may, for example, be applied for all of the synthesis steps. This highly efficient route allows simple and scalable purification based on the unique crystalline property of PEG in cold ether or alcohol that permits purification of PEG-derivatives from excessive reactants after each reaction steps without the need to use tedious column purification steps. The schemes for the synthesis of compounds 8, 9, 10, and 11 are shown in FIGS. 17A(i) and 17A(ii). These compounds differ in the number of Fmoc motifs [1 (compounds 8 and 9) vs. 2 (compounds 10 and 11)] and the use of FTS (compounds 8 and 10) or FTS-amide (compounds 9 and 11) as the hydrophobic domain of the micellar system.

Although PEG chains have been described as representative examples in the hydrophilic domains or segments of the carrier agents hereof, PEG chains may, for example, be replaced with other hydrophilic groups, including, for example, carboxyl or amine groups that have hydrophilic properties, or other hydrophilic polymers, sugars, etc.

The carrier agents/molecules hereof may, for example, be used alone in forming micelles with a drug as an inclusion complex or may, for example, be used in mixed-micelles, as added co-surfactant, together with other lipid components to form drug-loaded micelles, emulsions, creams, liposomes, spherulites, solid-lipid nanoparticles, hydrogels, cubic phase lipogels etc. In general, the amphiphilic or surfactant carrier agents hereof act as interface stabilizers for the compound/drug to enhance formulation stability and to increase drug loading capacity.

Carrier agents hereof may also be polymeric (including hydrophobic-hydrophilic or hydrophilic repeat units) made through copolymerization, or chemical modification, with drug-interaction segments/motifs. In the case of carrier agents including a hydrophilic domain and a hydrophobic domain attached to or conjugated with the drug-interactive domain, the drug-interactive segments/motifs may be incorporated either within the hydrophobic segments or at the boundary of hydrophilic and hydrophobic segments. For example, the hydrophilic segment may be, but is not limited to a PEG or a peptide sequence enriched with hydrophilic residues or hydrophilic derivatives thereof. As described above, the drug interactive motif may, for example, be at least one Fmoc group (for example, as a pending group of an amino acid residue).

The agents hereof may, for example, be "drug dispensers" in, for example, oral dosing agents to, for example, enhance drug absorption in gastric or intestine fluid and/or to increase residual time. The agents may also, for example, be used to increase penetration rate for topical or mucosal applications. Moreover, the agents may also be used as colloidal formulation agents for systemic injection.

Ligands specific for cell surface molecules may, for example be incorporated into the hydrophilic segment (for example, PEG) hereof at a terminus position to facilitate the rate or specificity of cellular uptake.

There are a number of attractive features of the carrier agents and formulation hereof as compared to other agents and systems. For example, carrier agents hereof (such as PEG-FTS conjugates) form small-sized mixed micelles (20~30 nm) with various types of anticancer agents including, for example, PTX, DOX, bicalutamide, etoposide, and curcumin. Such small sized micelles efficiently penetrate blood vessels and preferentially accumulate at tumor tissues, but not in other major organs as evidenced by in vivo imaging results. Moreover, carrier agents hereof clearly demonstrate a synergistic activity with, for example, PTX in several cancer cell lines tested and more effective therapeutic effects in vivo in both syngeneic and xenograft models. As described above, a biologically active hydrophobic compound such as FTS may be designed to couple with a hydrophilic compound such as PEG by ester linkages and/or other labile linkages, and is thus likely to be released from the conjugates hereof (for example, by the cellular esterase activities) following cellular uptake and to exhibit its synergistic antitumor activities with codelivered drugs. The release of the biologically active hydrophobic compound hereof or a biologically active analog or derivative thereof from the conjugates can be further facilitated via inclusion of a disulfide linkage. Formulations hereof such as $PEG_{5K}$-$FTS_2$/PTX also demonstrate excellent safety profiles. For example, the maximal tolerated dose (MTD, >140 mg PTX/kg) for PTX/$PEG_{5K}$-$FTS_2$ is significantly higher than those for most reported micellar PTX formulations. Further, introducing a compound/drug-interactive motif at the interfacial region (between the hydrophobic and hydrophilic domains of the carrier agent) can increase compound/drug loading capacity. For example, we have used Fmoc as a compound interactive agent or formulation chemophor that is highly effective in interacting with various types of therapeutic agents of diverse structures. Incorporation of a compound interactive agent including, for example, an Fmoc group can be readily achieved and has led to significant improvement in both drug loading capacity and formulation stability for PEG-FTS system. The Fmoc group is, for example, not known to associate with any harmful effects. Fmoc-containing peptides form hydrogels that are mild enough to support cells growth. Moreover, several Fmoc-containing dipeptides have shown anti-inflammatory properties. The carrier agents and formulation hereof are readily prepared and provide enhanced performance as compared to previously reported carrier agents and formulations formed therefrom.

Experimental Examples $PEG_5K$-$FTS_2$(L) and $PEG_5K$-$FTS_2$(S)

Materials.

Paclitaxel (98%) was purchased from AK Scientific Inc. (CA, USA). FTS was synthesized and purified following the published literature. 20 Pan-Ras Ab (Ab-3) was purchased from Calbiochem (La Jolla, Calif.). HRP-labeled goat anti-mouse IgG and the ECL chemiluminescence kit were purchased from Amersham Biosciences (Piscataway, N.J., USA). Dulbecco's phosphate buffered saline (DPBS) was purchased from Lonza (MD, USA). Poly(ethylene glycol) methyl ether (MeO-PEG-OH, Mw=5000 kDa), dimethyl sulfoxide (DMSO), 3-(4,5-dimethylthiazol-2-yl)-2,5-diphenyl tetrazolium bromide (MTT), trypsin-EDTA solution, Triton X-100, and Dulbecco's Modified Eagle's Medium (DMEM) were all purchased from Sigma-Aldrich (MO, USA). Fetal bovine serum (FBS) and penicillin-streptomycin solution were from Invitrogen (NY, USA).

Synthesis of $PEG_5K$-$FTS_2$(L) and $PEG_5K$-$FTS_2$(S) Conjugate.

$PEG_{5K}$-$FTS_2$(L) conjugate with a labile linkage was prepared via solution-phase condensation reactions from MeOPEG-OH with a molecular weight of 5000 (FIG. 1). We started by synthesizing carboxyl terminated PEG monomethyl ether (MeO-$PEG_{5K}$-COOH) from MeO-$PEG_{5K}$-OH (1 equiv) by a facile chemical reaction with succinic anhydride (5 equiv) and 4-(dimethylamino) pyridine (DMAP 5 equiv) in pyridine according to a reported method. 27 To obtain two hydroxyl group terminated PEG monomethyl ether (MeO-$PEG_{5K}$-$(OH)_2$), diethanolamine (3 equiv) was coupled onto the carboxylic group of MeO-$PEG_{5K}$-COOH (1 equiv) using Nhydroxysuccinimide (NHS 3.6 equiv)/dicyclohexylcarbodiimide (DCC 3.6 equiv) as coupling agent in chloroform overnight. The polymer was precipitated and washed by icecold ether three times, and concentrated under vacuum. MeOPEG$_{5K}$-$(OH)_2$, FTS, DCC, and DMAP were then dissolved in chloroform with a molar ratio of 1:6:3:0.3 and allowed to react overnight at room temperature. The solution was filtered and precipitated in ice-cold diethyl ether and ethanol twice respectively, and concentrated under vacuum. The powder was then dissolved in water and filtered through a filter with a pore size of 0.2 m. The final product was obtained by lyophilizing the filtrate. At the same time, we also prepared a $PEG_{5K}$-$FTS_2$(S) conjugate (Figure Si) with a stable amide linkage. MeO-$PEG_{5K}$-OH and (S)-2,6-Bis-tert-butoxycarbonylaminohexanoic acid (Boc-Lys(Boc)-OH) were dissolved in chloroform together with DCC and DMAP with a molar ratio of 1:3:1.5:0.3 and the mixture was left to react overnight at room temperature. PEGylated molecules were recovered from the mixture through three cycles of dissolution/reprecipitation with chloroform and ether, respectively. Boc groups were removed via the treatment with 50% (v/v) trifluoroacetic acid (TFA) in chloroform, and PEGylated molecules were precipitated and washed with ice-cold ether. Finally, FTS was coupled onto the N terminal group of MeO-$PEG_{5K}$-Lys-$(NH_2)_2$ (1 equiv) via NHS (3.6 equiv)/DCC (3.6 equiv) as described above. After the reaction was completed, the solution was precipitated in cold ether. $PEG_{5K}$-$FTS_2$(S) was similarly purified as that for $PEG_{5K}$-$FTS_2$(L).

Preparation of PTX-Loaded and Drug-Free Micelles.

PTX (10 mM in chloroform) and $PEG_{5K}$-$FTS_2$ (10 mM in chloroform) were mixed with various carrier/drug ratios. The organic solvent was removed by nitrogen flow to form a thin film of drug/carrier mixture. The film was dried under vacuum for 1 h to remove the remaining solvent. DPBS was added to hydrate the thin film and the drug-loaded micelles were formed. Unincorporated PTX (precipitate) was removed by filtering with a syringe filter (pore size: 0.22 m). The drug-free micelles were similarly prepared as described above.

$PEG_{5K}$-S—S-$FTS_2$ Conjugate

Materials.

Paclitaxel (98%) was purchased from AK Scientific Inc. (CA, USA). FTS and $PEG_{5K}$-$FTS_2$ conjugate were synthesized according to published literature.[6,7] Poly-(ethylene glycol) methyl ether (MeO-PEG-OH, MW=5000 kDa), dimethyl sulfoxide (DMSO), succinate anhydride, diethanolamine, trypsin-EDTA solution, Dulbecco's Modified Eagle's Medium (DMEM), and 3-(4,5-dimethylthiazol-2-yl)-2,5-diphenyl tetrazolium bromide (MTT) were all purchased from Sigma-Aldrich (MO, USA). Di-Boc-lysine, triethylamine (TEA), and trifluoroacetic acid (TFA) were obtained from Acros Organic (NJ, USA). Bis(2-hydroxyethyl) disulfide, dicyclohexylcarbodiimide (DCC), and N-hydroxysuccinimide (NHS) were purchased from Alfa Aesar (MA, USA). 4-(Dimethylamino)pyridine (DMAP) was purchased from Calbiochem-Novabiochem Corporation (CA, USA). All solvents used in this study were HPLC grade.

Cell Culture.

MCF-7 is a human breast carcinoma cell line. 4T1.2 is a mouse metastatic breast cancer cell line. HCT-116 is a human colon carcinoma cell line. PC-3 and DU-145 are human prostate cancer cell lines. All cell lines were cultured in DMEM containing 5% FBS and 1% penicillin-streptomycin at 37° C. in a humidified 5% $CO_2$ atmosphere.

Animals.

Female BALB/c mice, 4-6 weeks in age, were purchased from Charles River (Davis, Calif.). All animals were housed under pathogen-free conditions according to AAALAC guidelines. All animal-related experiments were performed in full compliance with institutional guidelines and approved by the Animal Use and Care Administrative Advisory Committee at the University of Pittsburgh.

Compound 1.

Bis(2-hydroxyethyl) disulfide (1.54 g, 10 mmol) was added to a solution of FTS (3.58 g, 10 mmol), DCC (3.09 g, 15 mmol), and DMAP (122 mg, 1 mmol) in $CH_2Cl_2$ (50 mL). The mixture was stirred at room temperature until TLC showed completion of reaction. The mixture was filtered through cotton and the filtrate was concentrated on a rotary evaporator. The residue was chromatographed (1:4 EtOAc/PE) on silica gel to afford the compound 1 (3.2 g, 6.5 mmol, 65%). $^1$H NMR (400 MHz, $CDCl_3$) δ 7.99-7.97 (m, 1H), 7.45-7.41 (m, 1H), 7.32-7.28 (m, 1H), 7.17-7.13 (m, 1H), 5.36-5.32 (m, 1H), 5.10-5.07 (m, 2H), 4.59 (t, J=6.8 Hz, 2H), 3.88-3.87 (m, 2H), 3.58-3.56 (m, 2H), 3.06 (t, J=6.8 Hz, 2H), 2.89 (t, J=6 Hz, 2H), 2.09-1.97 (m, 8H), 1.73 (s, 3H), 1.68 (s, 3H), 1.60 (s, 6H).

Compound 2.

Succinic anhydride (2 g, 20 mmol) was added to a solution of compound 1 (4.94 g, 10 mmol) and DMAP (2.44 g, 20 mmol) in $CHCl_3$ (50 mL), and the mixture was refluxed until TLC showed completion of reaction. The mixture was concentrated on a rotary evaporator and the residue was chromatographed (1:1 EtOAc/PE) on silica gel to afford compound 1 (3.2 g, 6.5 mmol, 65%). 1H NMR (400 MHz, $CDCl_3$) δ 7.99-7.97 (m, 1H), 7.41-7.38 (m, 1H), 7.29-7.27 (m, 1H), 7.14-7.10 (m, 1H), 5.30-5.27 (m, 1H), 5.06-5.03 (m, 2H), 4.54 (t, J=6.8 Hz, 2H), 4.33 (t, J=6.8 Hz, 2H), 3.55-3.53 (m, 2H), 3.03 (t, J=6.4 Hz, 2H), 2.89 (t, J=6.4 Hz, 2H), 2.62-2.61 (m, 4H), 2.04-1.92 (m, 8H), 1.69 (s, 3H), 1.64 (s, 3H), 1.55 (s, 6H).

Compound 5.

Compound 5 was synthesized from compound 3 following a published method. Zhang, X., et al. PEG-farnesylthiosalicylate conjugate as a nanomicellar carrier for delivery of paclitaxel. *Bioconjugate Chem.* 24, 464-472 (2013).

Compound 6.

DCC, DMAP, compound 2, and compound 5 were dissolved in $CH_2Cl_2$ with a molar ratio of 1:6:3:0.3 and allowed to react overnight at room temperature. The solution was filtered and precipitated in diethyl ether and ethanol twice, respectively. Compound 6 was obtained by further drying under vacuum.

Preparation and Characterization of PTX-Loaded PEG5-S—S-FTS2 Micelles. PTX-solubilized PEG5-S—S-FTS2 micelles were prepared via a solvent evaporation method following our published protocol. Briefly, PTX (10 mM in chloroform) and PEG5-S—S-$FTS_2$ conjugate (10 mM in chloroform) were mixed with various carrier/drug ratios. A film of drug/carrier mixture was formed by removed the organic solvent and the film was further dried under vacuum. PTX-loaded micelles were formed by adding DPBS to hydrate the thin film followed by gentle vortexing. The PTX loading efficiency was measured by high performance liquid chroma-tography (HPLC) (Alliance 2695-2998 system) as described in Zhang, X., et al. PEG-farnesylthiosalicylate conjugate as a nanomicellar carrier for delivery of paclitaxel. *Bioconjugate Chem.* 24, 464-472 (2013). Drug loading capacity (DLC) and drug loading efficiency (DLE) were calculated according to the equations set forth above.

Morphology, micelle size, and size distribution were assessed by transmission electron microscopy (TEM) and dynamic light scattering (DLS) following a published protocol. See Zhang, P., et al. Design and evaluation of a PEGylated lipopeptide equipped with drug-interactive motifs as an improved drug carrier. *AAPS J.* 16, 114-124 (2014). The critical micelle concentration (CMC) of $PEG_{5K}$-S—S-$FTS_2$ micelles was determined using pyrene as a fluorescence probe.

PEGsK-Fmoc-$FTS_2$ Conjugate.

Materials and Reagents.

Paclitaxel (98%) was purchased from AK Scientific Inc. (CA, USA). Doxorubicin (>99%) was purchased from LC Laboratories (MA, USA). 1,1'-dioctadecyl-3,3,3',3'-tetramethylindodicarbocyanine perchlorate (DiD) was purchased from Invitrogen (NY, USA). N-hydroxysuccinimide (NHS) and dicyclohexylcarbodiimide (DCC) were purchased from Alfa Aesar (MA, USA). 4-(dimethylamino) pridine (DMAP) was purchased from Calbiochem-Novabiochem Corporation (CA, USA). FTS was synthesized and purified following a published literature. See Marciano, D. et al., Farnesyl derivatives of rigid carboxylic acids-inhibitors of ras-dependent cell growth. *J. Med. Chem.* 38, 1267-72 (1995).

Synthesis of $PEG_5$K-Fmoc-$FTS_2$ Conjugate.

$PEG_{5K}$-Fmoc-$FTS_2$ was synthesized via solution condensation reactions from poly(ethylene glycol) methyl ether (mPEG-OH, Mw=5000 Da) ($mPEG_{5K}$-OH) (Scheme 1). $MPEG_{5K}$-OH was reacted with succinate anhydride (5 eq.) in $CH_2Cl_2$ overnight using DMAP (5 eq.) as a catalyst. The PEG derivative was precipitated with 10 volume of cold ether and washed with ether twice. Excess DMAP was removed by additional washes with cold ethanol (Yield=91%). The carboxy-terminated mPEG ($mPEG_{5K}$-COOH) was then reacted with tris(hydroxymethyl)aminomethane (Tris) in the presence of NHS (3 eq.) and DCC (3 eq.) in $CH_2Cl_2$ for one day, followed by a similar purification step as described above (Yield=92%). The two hydroxyl groups in the PEG-derivatized Tris were blocked by forming acetonide using p-Toluenesulfonic acid (TsOH) as a catalyst in acetone. Then, Fmoc group was coupled to the remaining OH of Tris via reaction with 9-fluorenylmethoxycarbonyl chloride (Fmoc-Cl) (2 eq.) and triethylamine (3 eq.) in $CH_2Cl_2$ overnight. PEGylated molecules were similarly purified as described above and acetonide group was removed by treatment with 1% TsOH in $CH_2Cl_2$ (Yield=50%, 2 steps). Finally, FTS (4 eq.) was coupled onto the PEGylated molecules with DCC (4 eq.) and DMAP (0.4 eq.) as the coupling reagents. The reaction mixture was filtered and precipitated with ether and ethanol twice, and concentrated under vacuum (Yield=85%). The powder was then dissolved in water and filtered through a filter with a pore size of 0.2 μm. The final product was obtained by lyophilizing the filtrate. $PEG_{5K}$-$FTS_2$ was synthesized following our reported method. Zhang, X.; et al., PEG-farnesylthiosalicylate conjugate as a nanomicellar carrier for delivery of paclitaxel. *Bioconjug. Chem.*, 24, 464-72 (2013).

Preparation and Characterization of PTX- and DOX-Loaded Micelles.

PTX (10 mM in chloroform) and $PEG_{5K}$-Fmoc-$FTS_2$ conjugate (10 mM in chloroform) were mixed with various carrier/drug ratios. After removing chloroform, a thin film of drug/carrier mixture was formed. PTX-loaded micelles were formed by adding DPBS to hydrate the thin film followed by gentle votexing. To load DOX into $PEG_{5K}$-Fmoc-$FTS_2$ micelle, DOX.HCl was first treated with triethylamine (3 eq.) in a mixture of chloroform ($CHCl_3$)/methanol (MeOH) (1:1, v/v) to remove HCl from DOX.HCl. DOX-loaded $PEG_{5K}$-Fmoc-$FTS_2$ micelles were then similarly prepared as described above. The PTX loading efficiency was quantified by high performance liquid chromatography (HPLC) as described in Zhang, X.; et al., PEG-farnesylthiosalicylate conjugate as a nanomicellar carrier for delivery of paclitaxel. *Bioconjug. Chem.*, 24, 464-72 (2013). The DOX loading efficiency was examined by Waters Alliance 2695 Separations Module combined with Waters 2475 Fluorescence Detector (Excitation: 490 nm; Emission: 590 nm; Gain: 3; Sensitivity (FUFS): 10000). Hibar 250-4 LiChrosorb RP-8 (5 micron) column (Sorbent Lot no. L59040432) was used and the mobile phase consisted of acetonitrile/water (52.5:47.5, v/v) with 2.5 mM $CH_3COONH_4$ and 0.05% (v/v) $CH_3COOH$. The flow rate of mobile phase was 1 mL/min and running time was 12 mins. Drug loading capacity (DLC) and drug loading efficiency (DLE) were calculated using the equations set forth above.

The mean diameter, morphology and size distribution of $PEG_{5K}$-Fmoc-$FTS_2$ micelles were assessed by dynamic light scattering (DLS) and transmission electron microscopy (TEM). The critical micelle concentration (CMC) of $PEG_{5K}$-Fmoc-$FTS_2$ micelles was determined using pyrene as a fluorescence probe.[34] The in vitro kinetics of DOX release from $PEG_{5K}$-Fmoc-$FTS_2$ micelles was examined by a dialysis method. See Xiong, X. B. et al., Enhanced intracellular delivery and improved antitumor efficacy of doxorubicin by sterically stabilized liposomes modified with a synthetic RGD mimetic. *J. Control. Release*, 107, 262-75 (2005). The hemolytic effect of $PEG_{5K}$-Fmoc-$FTS_2$ micelles was examined as described in Lu, J.; Huang, Y.; Zhao, W.; Marquez, R. T.; Meng, X.; Li, J.; Gao, X.; Venkataramanan, R.; Wang, Z.; Li, S., PEG-derivatized embelin as a nanomicellar carrier for delivery of paclitaxel to breast and prostate cancers. *Biomaterials*, 34, 1591-600 (2013).

Cell Culture and Animals.

4T1.2 (mouse metastatic breast cancer cell line), MCF-7 (human breast carcinoma cell line), and A549 (human lung adenocarcinoma epithelial cell line) were obtained from ATCC (VA, USA). HCT 116 (human colon carcinoma cell line) was kindly provided by Dr. Lin Zhang (University of Pittsburgh Cancer Institute). All cell lines were cultured in DMEM containing 5% FBS and 1% penicillin-streptomycin at 37° C. in a humidified 5% $CO_2$ atmosphere. Female BALB/c mice, 4-6 weeks in age, and CD-1 mice, 4-6 weeks in age, were purchased from Charles River (Davis, Calif.). Male nude mice, 6-8 weeks in age, were purchased from Harlan (Livermore, Calif.). All animals were housed under pathogen-free conditions according to AAALAC guidelines. All animal-related experiments were performed in full compliance with institutional guidelines and approved by the Animal Use and Care Administrative Advisory Committee at the University of Pittsburgh.

In Vitro Cytotoxicity Study.

The cytotoxicity of drugs (PTX and DOX) formulated in $PEG_{5K}$-Fmoc-$FTS_2$ micelles was assessed with several cancer cell lines and compared to Taxol and free DOX, respectively, by MTT assay. See Zhang, X.; et al., PEG-farnesylthiosalicylate conjugate as a nanomicellar carrier for delivery of paclitaxel. *Bioconjug. Chem.*, 24, 464-72 (2013). The cytotoxicity of free $PEG_{5K}$-$FTS_2$, $PEG_{5K}$-Fmoc-$FTS_2$ and FTS was also examined.

Maximum Tolerated Dose (MTD) Studies.

Groups of 4 female CD-1 mice were administered intravenously with free DOX (5, 10, 15, 20 mg DOX/kg), DOX-loaded $PEG_{5K}$-Fmoc-$FTS_2$ micelles (5, 10, 15, 20, 25, 30 mg DOX/kg), Taxol (15, 20, 25 mg PTX/kg), or PTX-loaded $PEG_{5K}$-Fmoc-$FTS_2$ micelles (50, 75, 100, 120, 140 mg PTX/kg), respectively. Changes in body weight and mouse survival were monitored daily for two weeks. The MTD was defined as the maximal dose that causes neither greater than 15% of body weight loss nor mouse mortality within two weeks after administration. See Lu, J.; Huang, Y.; Zhao, W.; Marquez, R. T.; Meng, X.; Li, J.; Gao, X.; Venkataramanan, R.; Wang, Z.; Li, S., PEG-derivatized embelin as a nanomicellar carrier for delivery of paclitaxel to breast and prostate cancers. *Biomaterials*, 34, 1591-600 (2013).

NIRF Optical Imaging.

Nude mice bearing bilateral s.c. PC-3 xenografts were i.v. injected with 200 μL of DiD-loaded $PEG_{5K}$-Fmoc-$FTS_2$ at a concentration of 0.4 mg/mL. At indicated times (0.5 h, 6 h, 24 h, 48 h, 72 h and 96 h), the mice were scanned using a Carestream Molecular Imaging System, In vivo Multispectral FX PRO, with the excitation at 630 nm and the emission at 700 nm using a 30 s exposure time. The mice were anesthetized by isoflurane inhalation before each imaging. After 96 h, the mice were euthanized by $CO_2$ overdose. The tumor and major organs were excised for ex vivo imaging.

Plasma Pharmacokinetics and Tissue Distribution.

DOX.HCl and DOX-loaded $PEG_{5K}$-Fmoc-$FTS_2$ micelles were injected into female BALB/c mice via tail vein at a dose of 5 mg DOX/kg. The blood samples were collected in heparinized tubes at different time points (3 min, 8 min, 15 min, 30 min, 1 h, 2 h, 4 h, 8 h, and 12 h) post-injection. The blood was centrifuged (2,500 rpm, 10 min) and plasma was collected for the analysis. DOX in plasma was extracted by extraction buffer (10% Triton X-100, deionized water, and isopropanol at a volumetric ratio of 1:2:15).[9] DOX was examined by HPLC using fluorescence detection. Non-compartmental pharmacokinetic analysis was done by WinNonlin. For tissue biodistribution study, DOX.HCl and DOX-loaded $PEG_{5K}$-Fmoc-$FTS_2$ were injected into female BALB/c mice bearing 4T1.2 breast tumor at a dose of 5 mg DOX/kg, respectively. At day 1 post-injection, tumor tissues and major organs were collected from the mice. The tissues were weighed and homogenized using Homogenizer PowerGen 500 (Fisher Scientific). The tissue solutions were mixed with the extraction buffer and DOX was extracted overnight at −20° C. The solutions were centrifuged (2,500 rpm, 10 min) and the supernatant was used for HPLC measurement. The concentrations of DOX in tissues were determined based on the standard curve of DOX in blood.

In Vivo Therapeutic Study.

Two tumor models (a syngeneic murine breast cancer model (4T1.2) and a human prostate cancer (PC-3) xenograft model) were used to assess the therapeutic activity of PTX or DOX formulated in $PEG_{5K}$-Fmoc-$FTS_2$ micelles. The breast cancer model was established by inoculation of 4T1.2 cells (1×10$^5$) in 200 μL PBS at the right flank of female BALB/c mice. Treatments were started when tumors achieved a volume of ~50 mm$^3$ and this day was designated as day 1. Then tumor-bearing mice were randomly divided into six groups (n=5) and administered i.v. with PBS (control), PEG$_{5K}$-Fmoc-FTS$_2$ micelles, Taxol (10 mg PTX/kg), PTX-loaded PEG$_{5K}$-Fmoc-FTS$_2$ micelles (10, 20 mg PTX/kg), and PTX-loaded PEG$_{5K}$-FTS$_2$ (10 mg PTX/kg), respectively on days 1, 3, 5, 8, 11 and 14. Free PEG$_{5K}$-Fmoc-FTS$_2$ micelles were given at the equivalent dosage of the carrier in the group of PTX-loaded PEG$_{5K}$-Fmoc-FTS$_2$ micelles (10 mg PTX/kg). The therapeutic effect of DOX-loaded PEG$_{5K}$-Fmoc-FTS$_2$ micelles (5, 10 mg DOX/kg) was similarly evaluated in 4T1.2 tumor model. Controls include PBS, PEG$_{5K}$-Fmoc-FTS$_2$ micelles, DOX.HCl (5 mg DOX/kg), liposomal DOX (5 mg DOX/kg), and DOX-loaded PEG$_{5K}$-FTS$_2$ (5 mg DOX/kg). Tumor sizes were measured with digital caliper three times per week and calculated as V=(L×W$^2$)/2, L=the longest diameter, W=the shortest diameter (mm). Each group was compared by relative tumor volume (RTV) (where RTV equals to the tumor volume divided by the initial tumor volume before treatment). Mice were sacrificed when the tumors developed ulceration or reached 2000 mm$^3$. The body weights of all mice from different groups were monitored every three days. The antitumor activity of PTX-loaded PEG$_{5K}$-Fmoc-FTS$_2$ micelles was further evaluated in a human prostate cancer xenograft model, PC-3. Different groups were similarly treated as described above on days 1, 3, 6, 9 and 12. Tumor size and body weight were monitored as described above.

Statistical Analysis.

Data are presented as mean±standard deviation (SD). Statistical analysis was performed by Student's t-test for comparison of two groups, and comparisons for multiple groups were made with one-way analysis of variance (ANOVA), followed by Newman-Keuls test if the overall P<0.05. In all statistical analysis, the threshold of significance was defined as P<0.05.

Synthesis of PEG$_5$—S—S-FTS$_2$ Conjugates.

FTS will react with diethanol disulfide using DCC and DMAP as a coupling agent to form compound 1, then the terminal hydroxyl group of compound 1 will react with succinate anhydride under DMAP to get compound 2 of FIG. 17A(i). FTS-amine will react with diethanol disulfide through triphosgene to form compound 3, then the hydroxyl group will react with succinate anhydride to get compound 2.

The PEG-lysyl(Fmoc)-lysyl(NH$_2$)$_2$ (6) will react with compound 2 or 4 using DCC and DMAP as a coupling agent to get compound 8 and 9 of FIG. 17A(ii). The PEG-lysyl-lysyl(Fmoc-NH$_2$)$_2$ (7) will react with compound 2 or 4 using DCC and DMAP as a coupling agent to get compound 10 and 11.

As illustrated in FIG. 17C, PEG-amine will react with Fmoc-lysine(Boc) using DCC and DMAP as a coupling agent, then the Boc group will be removed in the presence of TFA, diBoc-lysine will be coupled to amine using DCC and DMAP, the Boc group will be further removed by TFA. FTS will react with diethanol disulfide using DCC and DMAP as a coupling agent to form FTS-S—OH, and then the hydroxyl group will react with succinate anhydride to get FTS-S—CO$_2$H. FTS-S—CO$_2$H will couple with PEG-lysyl(Fmoc)lysyl-(NH$_2$)$_2$ to get the final compound.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A formulation, comprising:
a carrier agent formed by conjugating at least one biologically active hydrophobic compound selected from the group consisting of S-trans, trans-farnesylthiosalicylic acid, S-trans, trans-farnesylthiosalicylic acid amide (FTS-amide), S-trans, trans-farnesylthiosalicylic acid methylamide (FTS-MA) and S-trans, trans-farnesylthiosalicylic acid dimethylamide (FTS-DMA) with at least one hydrophilic polymer selected from the group consisting of a polyalkylene oxide, a polyvinylalcohol, a polyacrylic acid, a polyacrylamide, a polyoxazoline, a polysaccharide and a polypeptide,
wherein a plurality of the carrier agents are adapted to assemble into a structure and the at least one biologically active hydrophobic compound is conjugated with the at least one hydrophilic compound via a linkage which is labile in vivo, the linkage being selected from the group consisting of an ester linkage, a disulfide linkage, pH-sensitive linkage, ROS-sensitive linkage, or protease-sensitive linkage, and
a biologically active compound associated with the carrier agent.

2. The formulation of claim 1 wherein the at least one hydrophilic polymer is a polyalkylene oxide.

3. The formulation of claim 1 wherein the linkage comprises an ester linkage.

4. The formulation of claim 1 wherein the linkage comprises a disulfide linkage.

5. The formulation of claim 4 wherein the at least one hydrophilic polymer is a polyalkylene oxide.

6. The formulation of claim 5 wherein the polyalkylene oxide is a polyethylene glycol.

7. The formulation of claim 6 wherein the polyethylene glycol has a molecular weight of at least 1 KDa.

8. The formulation of claim 1 wherein the carrier agent provides a loading capacity for the biologically active hydrophobic compound of at least 10%.

9. The formulation of claim 2 wherein the biologically active compound is paclitaxel, doxorubicin, curcumin, bicalutamide, etoposide, camptothecin, a camptothecin analog, pemetrexed, docetaxel, epirubicin, doxorubicin, vinblastine, vindesine, etoposide, hydroxycamptothecin, irinotecan, mitoxantrone, tamoxifen, imatinib, gefitinib, erlotinib, sorafenib, and bortezomib.

10. The formulation of claim 2 wherein the biologically active compound is an anticancer agent.

11. The formulation of claim 2 wherein the carrier agent is formed by conjugating the at least one biologically active hydrophobic compound with at least one compound interactive agent and the at least one hydrophilic compound, the at least one compound interactive agent comprising at least one group that interacts with the biologically active compound.

12. The formulation of claim 11 wherein the at least one compound interactive agent comprises at least one of a fluorenylmethyloxycarbonyl group, a carbobenzyloxy group, an isobutoxycarbamate group, a naphthylacetyl group, a carbazole group, a quinolone group, an isoquinolone group, or a group which is a residue of a molecule selected from the group of the biologically active compound, a portion of the biologically active compound, (9H-fluoren-9-yl)methanamine, (9H-fluoren-9-yl)methanol, 9H-fluoren-9-amine, naphthalene, 1,1'-bi-2-naphthol (BI- NOL), camptothecin, a camptothecin analog, pemetrexed, docetaxel, paclitaxel, epirubicin, doxorubicin, vinblastine, vindesine, etoposide, hydroxycamptothecin, irinotecan, mitoxantrone, tamoxifen, tretinoin, curcumin, imatinib, gefitinib, erlotinib, sorafenib, and bortezomib, or a derivative thereof.

13. The formulation of claim 11 wherein the at least one compound interactive agent comprises at least one fluorenylmethyloxycarbonyl group or a derivative thereof.

14. The formulation of claim 1 wherein the plurality of the carrier agents are adapted to assemble into micelles.

15. The formulation of claim 14 wherein the average size of the micelles is less than 100 nm.

16. The formulation of claim 14 wherein the average size of the micelles is in the range of 20-30 nm.

17. A method of forming a formulation according to claim 1 comprising:
forming the carrier agent by conjugating the at least one biologically active hydrophobic compound with the at least one hydrophilic compound, wherein a plurality of the carrier agents are adapted to assemble into a structure and the at least one biologically active hydrophobic compound is conjugated with the at least one hydrophilic compound via the linkage which is labile in vivo, and associating a biologically active compound with the carrier agent.

18. A method of delivering a biologically active compound to a patient, comprising:
delivering to the patient a composition comprising a compound according to claim 1.

19. A composition formed by:
conjugating at least one biologically active hydrophobic compound selected from the group consisting of farnesylthiosalicylic acid, S-trans, trans-farnesylthiosalicylic acid, S-trans, trans-farnesylthiosalicylic acid amide (FTS-amide),S-trans, trans-farnesylthiosalicylic acid methylamide (FTS-MA) and S-trans, trans-farnesylthiosalicylic acid dimethylamide (FTS-DMA) with at least one hydrophilic polymer selected from the group consisting of a polyalkylene oxide, a polyvinyl-alcohol, a polyacrylic acid, a polyacrylamide, a polyoxazoline, a polysaccharide and a polypeptide via at least one linkage which is cleavable in vivoo, the linkage being selected from the group consisting of an ester linkage, a disulfide linkage, pH-sensitive linkage, ROS-sensitive linkage, or protease-sensitive linkage.

20. The composition of claim 19 wherein the composition is formed by conjugating the at least one biologically active hydrophobic compound with at least one compound interactive agent and the at least one hydrophilic polymer, the at least one compound interactive agent comprising at least one group that interacts with a biologically active compound to be delivered via the composition.

21. The composition of claim 20 wherein the at least one compound interactive agent comprises at least one of a fluorenylmethyloxycarbonyl group, a carbobenzyloxy group, an isobutoxycarbamate group, a naphthylacetyl group, a carbazole group, a quinolone group, an isoquinolone group, or a group which is a residue of a molecule selected from the group of the biologically active compound, a portion of the biologically active compound, (9H-fluoren-9-yl)methanamine, (9H-fluoren-9-yl)methanol, 9H-fluoren-9-amine, naphthalene, 1,1'-bi-2-naphthol (BI-NOL), camptothecin, a camptothecin analog, pemetrexed, docetaxel, paclitaxel, epirubicin, doxorubicin, vinblastine, vindesine, etoposide, hydroxycamptothecin, irinotecan, mitoxantrone, tamoxifen, tretinoin, curcumin, imatinib, gefitinib, erlotinib, sorafenib, and bortezomib, or a derivative thereof.

22. The composition of claim 21 wherein the at least one compound interactive agent comprises at least one fluorenylmethyloxycarbonyl group or a derivative thereof.

23. The composition of claim 21 wherein a plurality of the compositions are adapted to assemble into a micelle.

24. The composition of claim 21 wherein the at least one linkage comprises an ester linkage.

25. The composition of claim 21 wherein the at least one linkage comprises a disulfide linkage.

* * * * *

UNITED STATES PATENT AND TRADEMARK OFFICE
CERTIFICATE OF CORRECTION

PATENT NO. : 9,855,341 B2  
APPLICATION NO. : 14/625873  
DATED : January 2, 2018  
INVENTOR(S) : Song Li et al.

Page 1 of 1

It is certified that error appears in the above-identified patent and that said Letters Patent is hereby corrected as shown below:

On the Title Page

Item (54) and in the Specification, Column 1, Line 2, in the title, delete "FARNESYLTHIOSALYCYLIC" and insert --FARNESYLTHIOSALICYLIC--

Signed and Sealed this  
Twenty-first Day of August, 2018

Andrei Iancu  
*Director of the United States Patent and Trademark Office*